United States Patent [19]
Farb

[11] Patent Number: 6,083,941
[45] Date of Patent: *Jul. 4, 2000

[54] INHIBITION OF NMDA RECEPTOR ACTIVITY BY PREGNENOLONE SULFATE DERIVATIVES

[75] Inventor: David H. Farb, Cambridge, Mass.

[73] Assignee: Trustees of Boston University, Boston, Mass.

[ * ] Notice: This patent is subject to a terminal disclaimer.

[21] Appl. No.: 09/012,910

[22] Filed: Jan. 23, 1998

Related U.S. Application Data

[63] Continuation of application No. PCT/US96/12198, Jul. 24, 1996, which is a continuation-in-part of application No. 08/559,442, Nov. 15, 1995, Pat. No. 5,888,996, which is a continuation-in-part of application No. 08/507,757, Jul. 26, 1995, abandoned

[60] Provisional application No. 60/001,439, Jul. 24, 1995.

[51] Int. Cl.$^7$ ...................................................... A61K 31/56
[52] U.S. Cl. .......................... 514/177; 514/178; 514/179; 514/182
[58] Field of Search ................................... 514/177, 178, 514/179, 182

[56] References Cited

U.S. PATENT DOCUMENTS

| 5,212,167 | 5/1993 | Farb | 514/178 |
| 5,366,968 | 11/1994 | Farb | 514/178 |

FOREIGN PATENT DOCUMENTS

| WO 93/04687 | 9/1991 | WIPO . |
| WO 93/05786 | 4/1993 | WIPO . |
| WO 94/27608 | 12/1994 | WIPO . |

OTHER PUBLICATIONS

CA 117: 185114 (Maione et al.) abstract, 1992.
Irwin, R.P., et al., "Steroid Potentiation and Inhibition of N–Methyl–D–Aspartate Receptor–Mediated Intracellular Ca++ Responses: Structure–Activity Studies," *J. Pharm. and Experimental Therapeutics*, 271(2) :677–682 (1994).
Lan, N.C., et al., "Neuroactive Steroid Actions at the GABA$_A$ Receptor," *Hormones and Behavior*, 28:537–544 (1994).
Park–Chung, M., et al., "3α–Hydroxy–5β–pregnan–20–one Sulfate: A Negative Modulator of the NMDA–Induced Current in Cultured Neurons," *Molecular Pharmacology*, 46:146–150 (1994).
Wong, M., and Moss, R.L., "Patch–Clamp Analysis of Direct Steroidal Modulation of Glutamate Receptor–Channels," *Journal of Neuroendocrinology*, 6:347–355 (1994).
Bowlby, M.R., "Pregnenolone Sulfate Potentiation of N–Methyl–D–Aspartate Receptor Channels in Hippocampal Neurons," *Mol. Pharmacol.*, 43(5) :813–819 (1993).
Wieland, S., et al., "Anxiolytic Activity of the Progesterone Metabolite 5α–pregnan–3α–ol–20–one," *Brain Research*, 565:263–268 (1991).
Wu, F.–S., et al., "Pregnenolone Sulfate: A Positive Allosteric Modulator at the N–Methyl–D–Aspartate Receptor," *Molecular Pharmacology*, 40:333–336 (1991).
Belelli, D., et al., "Anticonvulsant Profile of the Progesterone Metabolite 5α–pregnan–3α–ol–20–one," *European J. of Pharmacology*, 166:325–329 (1989).
Gyermek, L., et al., "Structure–Activity Relationship of Some Steroidal Hypnotic Agents," *Steroids*, CCX., 11:117–125 (1968).

*Primary Examiner*—Rebecca Cook
*Attorney, Agent, or Firm*—Kevin M. Farrell

[57] ABSTRACT

The present invention relates to a method of inhibiting N-methyl-D-aspartate (NMDA) glutamate receptor-mediated ion channel activity (NMDA receptor activity), comprising contacting a neuronal cell (e.g., hippocampal neuron, spinal cord cell) with an effective amount (e.g., 1 to 500 $\mu$M) of a derivative of pregnenolone sulfate. Derivatives of pregnenolone sulfate that inhibit NMDA receptor activity include pregnenolone sulfate derivatives in which the A ring includes at least one double bond; PS in which the A ring is fully unsaturated; PS derivatives in which the double bond at the C5–C6 position is reduced; and PS in which the moiety at the C3, C5, C6, C7, C11, C17, C20 and/or C21 position is modified. It further relates to PS derivatives which have modifications at other positions (e.g., C10, C10, C13, C18, C19), alone or in combination, and are inhibitors of NMDA receptor activity. The present invention also relates to a method of modulating or altering (e.g., potentiating; inhibiting) excitatory glutamate-mediated synaptic activity comprising contacting neurons with pregnenolone sulfate and derivatives of pregnenolone sulfate. The present invention also relates to a method of treating a disease associated with L-glutamate-induced NMDA receptor activation selected from the group consisting of: neuropathic pain, drug withdrawal/dependency, epilepsy, glaucoma, chronic neurodegenerative diseases, amyotrophic lateral sclerosis, anxiety disorders, brain cell death, ischaemia, stroke, trauma in a host comprising administering to the host an effective amount of a derivative of pregnenolone sulfate.

19 Claims, 14 Drawing Sheets

INHIBITION OF NMDA RECEPTOR ACTIVITY BY PREGNENOLONE SULFATE DERIVATIVES

RELATED APPLICATIONS

This is a Continuation application of PCT/US96/12198 filed Jul. 24, 1996 which is a Continuation-in-Part of U.S. application Ser. No. 08/559,442 filed Nov. 15, 1995 U.S. Pat. No. 5,888,996, both entitled "Inhibition of NMDA Receptor Activity and Modulation of Glutamate-Mediated Synaptic Activity" by David H. Farb, which is a Continuation-in-part of U.S. application Ser. No. 08/507,757 filed Jul. 26, 1995 abandoned entitled "Inhibition of NMDA Receptor Activity" by David H. Farb, which claims the benefit of U.S. Provisional Application No. 60/001,439, filed on Jul. 24, 1995, entitled "3α-Hydroxy-5β-Pregnan-20-One Sulfate: A Negative Modulator of the NMDA-Induced Current in Cultured Neurons" by David H. Farb. The entire teachings of all of the related applications are expressly incorporated herein by reference.

BACKGROUND OF THE INVENTION

L-Glutamate is thought to be the major excitatory neurotransmitter in the vertebrate central nervous system and is known to activate at least three major, pharmacologically distinct classes of glutamate-gated ion channels: N-methyl-D-aspartate (NMDA), α-amino-3-hydroxy-5-methyl-4-isoxazole-propionate (AMPA), and kainate receptors. These three inotropic receptors are named according to their selective agonists.

NMDA receptors have attracted particular attention because of their importance in normal brain function and in pathophysiological conditions such as epilepsy and cerebral ischemia (Rothman, S. M. and Olney, J. W., *Trends Neurosci.*, 10:299–302 (1987)). The NMDA receptor appears to be essential for the induction of long-term potentiation (Collingridge, G. L. and Bliss, T. V. P., *Trends Neurosci.*, 10:288–293 (1987)), a proposed underlying mechanism for learning and memory (Madison, D. V., et al., *Annu. Rev. Neurosci.*, 14:379–397 (1991)), ischemic cell death, epilepsy, and other neurological disorders (Simon, R. P., et al., *Science* 226:850–852 (1984); Choi, D. W., *J. Neurosci.* 10:2493–2501 (1990)) such as hypoxic neuronal damage (Simon, R., et al., *Science*, 226:850–852 (1984)), schizophrenia (Carlsson, M., et al., *Trends Neurosci.*, 13:272–276 (1990); Watchel, H., et al., *Trends Pharmacol. Sci.*, 11:219–220 (1990)) and excitotoxicity (Onley, J., et al., *Brain Res.*, 221:207–210 (1981)). The integral channel of the NMDA receptor is permeable to $Na^+$, $K^+$, and $Ca^{2+}$. NMDA receptor activation thus increases intracellular $Ca^{2+}$ in neuronal cells, and this process is thought to evoke glutamate-induced neurotoxicity (Madison, D. V., et al., *Annu. Rev. Neurosci.*, 14:379–397 (1991)).

Thus, inhibition of NMDA receptor activity would be useful for protecting against various disorders including glutamate-induced neurotoxicity.

SUMMARY OF THE INVENTION

The present invention relates to a method of inhibiting N-methyl-D-aspartate (NMDA) glutamate receptor-mediated ion channel activity (NMDA receptor activity), comprising contacting a neuronal cell (e.g., hippocampal neuron, spinal cord cell) with an effective amount (e.g., 1 to 500 μM) of a derivative of pregnenolone sulfate (PS). Derivatives of pregnenolone sulfate that inhibit NMDA receptor activity include PS derivatives in which the A ring includes at least one double bond; PS in which the A ring is fully unsaturated; PS derivatives in which the double bond at the C5–C6 position is reduced; and PS in which the moiety at the C3, C5, C6, C7, C11, C17, C20 and/or C21 position is modified. As defined herein, PS derivatives include these modifications to PS alone or in combinations thereof. It further relates to PS derivatives which have modifications at other positions (e.g., C10, C13, C16, C18, C19), alone or in combination, and are inhibitors of NMDA receptor activity. It is reasonable to expect that other PS derivatives such as: PS derivtives in which there are one or more double bonds in rings B, C or D; PS derivatives in which there is deletion of one or more carbon atoms in the A, B, C and/or D rings; and/or PS derivatives in which one or more carbon atoms bridging, for example, C19 and C3, C19 and C5 and/or C19 and C6, is added. The PS derivatives differ from PS in at least one position.

In one embodiment the present invention relates to a method for inhibiting NMDA glutamate receptor mediated ion-channel activity comprising contacting a neuronal cell with an effective amount of a derivative of pregnenolone sulfate wherein the derivative is selected from the group consisting of: 3α-hydroxy-5β-pregnan-20-one sulfate (5β3αS), 3β-hydroxy-5β-pregnan-20-one sulfate (5β3βS), 3α-hydroxy-5α-pregnan-20-one sulfate (5α3αS), 3α-hydroxy-5α-pregnan-20-one hemisuccinate (5β3αHS), 5α3αHS, 5β3βHS, 17β-estradiol-3-hemisuccinate (17βE(3)HS), 17β-estradiol-17-hemisuccinate (17βE(17)HS), 17βE(3,17)diHS, 17β estradiol, 11β-OH-pregnenolone sulfate and androsterone sulfate.

The present invention also relates to a method of inhibiting toxic effects associated with activation of the NMDA receptor in neurons (e.g., hippocampal neurons, spinal cord cells), comprising contacting the neurons with a derivative of pregnenolone sulfate selected from the group consisting of: 5β3αS, 5β3βS, 5α3αS, 5β3αHS, 5α3αHS, 5β3βHS, 17β-estradiol-3-hemisuccinate (17βE(3)HS), 17β-estradiol-17-hemisuccinate (17βE(17)HS), 17βE(3,17)diHS, 17β estradiol, 11β-OH-pregnenolone sulfate and androsterone sulfate.

Thus, the ability to selectively inhibit the NMDA receptor across nerve cell membranes offers the means for pharmacological intervention in various glutamate-induced conditions such as excitotoxicity, epilepsy, cerebral ischemia and stroke.

The present invention also relates to a method of modulating or altering (e.g., potentiating; inhibiting) excitatory glutamate-mediated synaptic activity comprising contacting neuronal cells with pregnenolone sulfate or a derivative of pregnenolone sulfate. In one embodiment, the invention relates to a method of potentiating excitatory glutamate-mediated synaptic activity comprising contacting neuronal cells with pregnenolone sulfate or a derivative of pregnenolone sulfate (e.g., dehydroepiandrosterone sulfate). In another embodiment, the invention relates to a method of inhibiting excitatory glutamate-mediated synaptic activity comprising contacting neuronal cells with a derivative of pregnenolone sulfate (e.g. 5β3αS).

The ability to modulate the excitatory glutamate-mediated synaptic activity offers the means for pharmacological intervention in various glutamate-mediated synaptic activities such as neuropathic pain, drug withdrawal/dependency, epilepsy, chronic neurodegenerative diseases (Parkinson's Disease, Alzheimer's Disease, AIDS, Huntington's Disease) amyotrophic lateral sclerosis and anxiety disorders. Thus, the present invention also relates to a method of treating in an individual (e.g., human) a disease or condition associated with L-glutamate-induced NMDA receptor activation by administering to the individual an effective amount of a derivative of pregnenolone sulfate. The diseases and conditions include neuropathic pain, drug withdrawal/dependency, epilepsy, glaucoma, chronic neurodegenerative diseases, amyotrophic lateral sclerosis, anxiety disorders, brain cell death, ischaemia, stroke, trauma to brain, spinal cord, peripheral ganglia or the enteric nervous system.

The compounds described herein can also be used as anti-convulsants, sedative or hypnotic agents or as muscle relaxants.

In addition, the present invention relates to a method of identifying an agent or compound which modulates glutamate-mediated synaptic activity. For example, neurons are contacted with a steroid described herein which modulates (potentiates or inhibits) excitatory glutamate-mediated synaptic activity and the affinity of the steroid to its receptor (NMDA) is established. The compound to be assessed is added and assessed for its ability to compete for the binding site of the steroid.

DETAILED DESCRIPTION OF THE INVENTION

Figure 1:
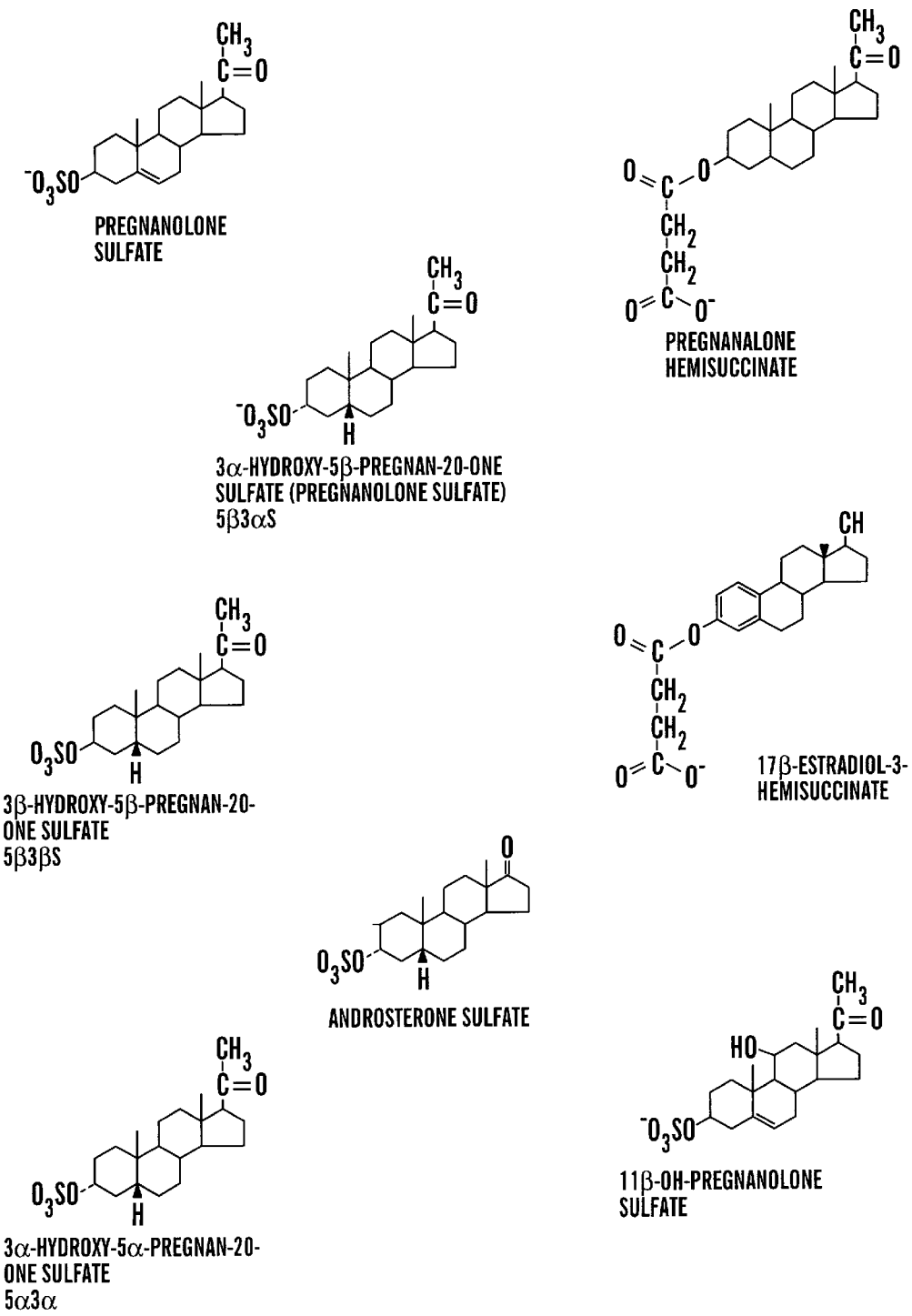
FIG. 1 is a diagram showing the general structures of pregnenolone sulfate, 3α-hydroxy-5β-pregnan-20-one sulfate (5β3αS), 3β-hydroxy-5β-pregnan-20-one sulfate (5β3βS), 3α-hydroxy-5α-pregnan-20-one sulfate (5α3αS), 5β3α hemisuccinate, 17β-estradiol 3-hemisuccinate, 11β-OH-pregnenolone sulfate and androsterone sulfate.

The present invention is based on the discovery that derivatives of pregnenolone sulfate (PS), a potentiator of NMDA receptor activity, inhibit NMDA receptor activity. Secondly, inhibition is exerted through a site and/or mechanism distinct from that of potentiation. Derivatives of pregnenolone sulfate that inhibit NMDA receptor activity include PS derivatives in which the A ring includes at least one double bond; PS in which the A ring is fully unsaturated; PS derivatives in which the double bond at the C5–C6 position is reduced; and PS in which the moiety at the C3, C5, C6, C7, C11, C17, C20 and/or C21 position is modified. As defined herein, PS derivatives include these modifications to PS alone or in combinations thereof. It further relates to PS derivatives which have modifications at other positions (e.g., C10, C13, C16, C18, C19), alone or in combination, and are inhibitors of NMDA receptor activity. It is reasonable to expect that other PS derivatives such as: PS derivatives in which there are one or more double bonds in rings B, C or D; PS derivatives in which there is deletion of one or more carbon atoms in the A, B, C and/or D rings; and/or PS derivatives in which one or more carbon atoms bridging, for example, C19 and C3, C19 and C5 and/or C19 and C6, is added. The PS derivatives differ from PS in at least one position. Examples of PS derivatives include 5β3αS, 5β3βS, 5α3αS, 5β3αHS, 5α3αHS, 5β3βHS, 17β-estradiol-3-hemisuccinate (17βE(3)HS), 17β-estradiol-17-hemisuccinate (17βE(17)HS), 17βE(3,17)diHS, 17β estradiol, 11β-OH-pregnenolone sulfate and androsterone sulfate.

In the methods of the present invention, a derivative of pregnenolone sulfate is contacted with a neuronal cell. A neuronal cell includes those from the central nervous system (e.g., spinal cord cell, hippocampal cell). Additionally, any cell in the nervous system, such as a glial cell bearing an NMDA receptor would naturally be an expected target of PS derivatives, as described herein.

In the methods of the present invention, a sufficient amount of a pregnenolone sulfate derivative is administered to an individual (e.g., human) to inhibit NMDA receptor activity (i.e., an effective amount). Preferably the concentration of the pregnenolone sulfate derivative is about 1–500 μM. A more preferred range is from about 50 to about 250 μM.

As used herein the term "inhibition of NMDA receptor activity" includes partial or total inhibition of the effects of NMDA receptor activity (e.g., excitotoxicity).

In addition to the derivatives of pregnenolone sulfate described herein, one skilled in the art can predict with a high degree of certainty that other modifications of these pregnenolone sulfate derivatives are also useful for inhibiting the NMDA receptor-mediated ion channel activity. These modifications can be in addition to or independent of (in lieu of) those at the A ring, the C5–C6 double bond, the C3, C10, C11 or C13 position. Those skilled in the art recognize that pregnenolone sulfate derivatives with modifications at other positions such as the C5, C7, C10, C16, C17, C18, C19, C20 and/or C21 position are inhibitors of NMDA receptor activity. In addition, some modifications can increase the inhibitory effects on the NMDA receptor and, as a result, reduced concentrations of these derivatives are needed. For example, the polar OH group of 11β-OH-pregnenolone sulfate can be substituted with an aliphatic or aromatic alcohol, thiol, or amine. Alternatively, the 11 hydroxy oxygen atom could participate in an ether linkage to the aliphatic or aromatic alcohol, thiol or amine.

Such derivatives include, for example, derivatives in which the sulfate at position 3 of the steroid skeleton is replaced by an alkyl sulfate. The alkyl sulfates include, for example, methyl, ethyl, butyl and propyl sulfates.

Alternatively, steroid sulfate derivatives in which the sulfate at position 3 of the steroid skeleton is replaced with a phosphate, methylthiophosphonothioate, or sulfamate can be used. In the instance of the sulfamate, linkage to the parent steroid is through an amino group substituted for the hydroxyl at carbon 3.

Alternatively, steroid sulfate derivatives in which the sulfate at position 3 of the steroid skeleton is replaced with a sulfonate can be used. These include, for example, methyl, ethyl, propyl, isopropyl and dimethyl sulfonates.

Additionally, derivatives in which the sulfate at position 3 of the parent steroid skeleton is replaced by an alkyl or aryl sulfate that is joined to the steroid skeleton via an ether, thioether, nitrogen atom, or carbon—carbon bond, and in which the sulfate is separated from the steroid by an alkyl or aryl group can be used. Alternatively, derivatives in which the alkyl sulfate at position 3 of the steroid skeleton is replaced with an alkyl or aryl phosphate, methylthiophosphonothioate, sulfonate, or sulfamate can be used. For example, one or more sulfate or sulfonate groups can be added to the benzoate moiety of 17β-estradiol benzoate or pregnenolone benzoate.

A third useful class of derivatives have a dicarboxylic acid in place of the sulfate at position 3 linked to the parent steroid skeleton by an ester bond. The dicarboxylic acids include alkyl and aryl dicarboxylates. The alkyl include, for example, methyl, ethyl, propyl, butyl, pentyl, hexyl, heptyl and octyl, and the aryl dicarboxylates include ortho, para and meta benzoates. For example, one or more carboxylate groups could be added to the benzoate moiety of 17β-estradiol benzoate or pregnenolone benzoate.

A fourth useful class of derivatives have one or more negative charges introduced by, for example, a carboxylate, sulfate, phosphate, sulfonate or methylthiophosphonothioate derivative of a sugar in place of the sulfate at position 3 of the parent steroid (i.e., pregnenolone sulfate). These include, for example, pregnenolone-3-D(or L)-glucosiduronate or pregnenolone-3-D(or L)-phosphoglucosiduronate. Specific examples of the modifications discussed above include 3α-hydroxy-16-imino-5β-17-aza-androstane-11-one or 3α-hydroxy-5α-pregnane-11,20-dione hemisuccinate.

Other specific examples of compounds which could be used in the present invention include: pregnenolone phosphate, pregnenolone formate, pregnenolone hemioxalate, pregnenolone hemimalonate, pregnenolone hemiglutarate, 20-oxopregn-5-en-3β-yl carboxymethyl ether, (plus carboxyalkyl ether counterparts to active carboxylic acid derivatives), 3α-hydroxypregn-5-en-20-one sulfate, 3-hydroxy-19-norpregna-1,3,5(10)-trien-20-one, 3-hydroxy-19-norpregna-1,3,5(10),6,8-pentaen-20-one, 17α-isopregnenolone sulfate, 17-acetoxypregnenolone sulfate, 21-hydroxypregnenolone sulfate, 20β-acetoxy-3β-hydroxypregn-5-ene-sulfate, pregnenolone sulfate 20-ethyleneketal, pregnenolone sulfate 20-carboxymethyloxime, 20-deoxypregnenolone sulfate, 21-acetoxy-17-hydroxypregnenolone sulfate, 17-propyloxypregnenolone sulfate, 17-butyloxypregnenolone sulfate, 21-thiol esters of PS, pyridinium, imidazolium, 6-methylpregnenolone sulfate, 6,16α-dimethylpregnenolone sulfate, 3β-hydroxy-6-methylpregna-5,16-dien-20-one sulfate, 3β-hydroxy-6,16-dimethylpregna-5,16-dien-20-one sulfate, 3β-hydroxypregna-5,16-dien-20-one sulfate, diosgenin sulfate, 3β-hydroxyandrost-5-en-17β-carboxylic acid methyl ester sulfate, 3α hydroxy-5β-pregnan 20 one formate, 3α-hydroxy-5β-pregnan-20-one hemioxalate, 3α-hydroxy-5β-pregnan-20-one hemimalonate, 3α-hydroxy-5β-pregnan-20-one hemisuccinate, 3α-hydroxy-5β-pregnan-20-one hemiglutarate, estradiol-3-formate, estradiol-3-hemioxalate, estradiol-3-hemimalonate, estradiol-3-hemisuccinate, estradiol-3-hemiglutarate (plus corresponding carboxy, alkyl, ethers of active compounds), estradiol-17-methyl ether, estradiol-17-formate, estradiol-17-hemioxalate, estradiol-17-hemimalonate, estradiol-17-hemisuccinate, estradiol-17-hemiglutarate, estradiol 3-methyl ether, 17-deoxyestrone, and 17β0hydroxyestra-1,3,5(10)-trien-3-yl carboxymethyl ether.

The neurosteroid pregnenolone sulfate acts as a positive allosteric modulator at the NMDA receptor and inhibits the kainate, the AMPA, the glycine, and the γ-aminobutyric acid (GABA) responses of chick spinal cord neurons (Wu, F. S., et al., *Mol. Pharmacol.* 40:333–336 (1991)). It was surprising that particular derivatives of pregnenolone sulfate, such as 5β3αS (FIG. 1) inhibit the NMDA receptor-induced current.

The NMDA receptor is subject to modulation through several pharmacologically distinct sites (Monaghum, D. T., et al., *Annu. Rev. Pharmacol.,* 29:365–402 (1989); Wong, E. H. F. and Kemp, J. A., *Annu. Rev. Pharmacol. Toxicol.,* 81:401–525 (1991)), including those for glycine, $Mg^{2+}$, and polyamines (Ransom, R. W. and Stec, N. L., *J. Neurochem.,* 51-830–836 (1988)). Moreover, the dissociative anesthetics dizocilpine (MK-801), phencyclidine (PCP), and ketamine all produce a voltage-dependent and use-dependent blockade of ion channel activity (Hucttner, J. E. and Bean, B. P., *Proc. Natl. Acad. Sci. USA,* 85:1307–1311 (1988); Lerma, J., et al., *Neurosci. Lett.,* 123:187–191 (1991)).

As described in Example 1, 5β3αS inhibits the NMDA-induced response by a voltage- and agonist-independent, noncompetitive mechanism that is different from that of open channel blockers such as MK-801. In addition, androsterone sulfate, inhibited the NMDA-induced response (see Table 1).

5β3αS, a sulfated form of naturally occurring 5β3α, inhibits both the NMDA and the non-NMDA receptor-mediated responses as measured by whole cell voltage clamp recordings. 100 μm 5β3αS rapidly and reversibly inhibits the response to 30 μm NMDA by 66%, 50 μM kainate by 37%, and 25 μM AMPA by 29%. Application of 60 μM nonsulfated 5β3α does not produce any significant effect on the NMDA response, demonstrating that the sulfate moiety is important for the effect of 5β3αS on the NMDA response. The effect of 5β3αS on the NMDA response is concentration dependent; the $EC_{50}$ is 62 μM. 5β3αS reduces the maximum NMDA response with little effect on the NMDA $EC_{50}$ indicating that antagonism of the NMDA response by 5β3αS is noncompetitive. The fact that 5β3αS inhibition of the NMDA response is neither agonist nor voltage dependent demonstrates that 5β3αS does not act as an open channel blocker.

Based on the ability of 5β3αS to exhibit a robust inhibitory effect on the NMDA response, the mechanism of action of 5β3αS on the NMDA response was further studied. As described in Example 1, inhibition of the NMDA response by 5β3αS is not reduced by the addition of a maximal concentration (10 μM) of glycine, indicating that 5β3αS does not act via the glycine recognition site. The inhibitory action of 5β3αS on the NMDA and non-NMDA receptors provides a basis for inhibiting glutamate receptor-induced seizures and excitotoxic cell death.

Example 2 describes further characterization of the inhibitory effect of pregnenolone sulfate derivatives on the NMDA response using 5β3βS. The data in Example 2 demonstrate that inhibition of the NMDA response occurs at a specific site which is distinct from other known recognition sites of the NMDA receptor (e.g., NMDA (or glutamate) glycine, polyamine, arachidonic acid and redox recognition sites). It is also likely that the site of action of negative modulators of the NMDA receptor such as 5β3βS, a negatively charged organic molecule, is distinct from the zinc recognition site of the NMDA receptor, since zinc is a divalent cation. In addition, the data in Example 2 demonstrate that positive modulators (e.g., pregnenolone sulfate) and negative modulators (e.g., 5β3βS, 5β3αS) of the NMDA response produce their respective effects by acting through different sites and/or pathways. The results provide strong support for the existence of a novel extracellular steroid inhibitory site on the NMDA receptor.

Example 3 describes additional pregnenolone sulfate derivatives which were examined by electrophysiology for inhibition of NMDA receptor activity. In addition, as described in Example 4, pregnenolone sulfate derivatives which inhibit NMDA receptor activity also protect against the excitotoxicity effects associated with persistent NMDA receptor activity.

Associated with stroke, hypoxia neuronal damage and ischemia is cell death thought to result from effects associated with activation of the NMDA receptor by L-glutamate. Therefore, it is possible to prevent cell death by interfering with L-glutamate-induced NMDA-receptor activation. The present invention relates to a method of reducing neuronal cell death resulting from L-glutamate activation of the NMDA receptor, comprising contacting neuronal cells with a derivative of pregnenolone sulfate selected from the group consisting of: pregnenolone sulfate in which the A ring includes at least one double bond; PS in which the A ring is fully unsaturated; PS derivatives in which the double bond at the C5–C6 position is reduced; and PS in which the moiety at the C3, C5, C6, C7, C11, C17, C20 and/or C21 position; and combinations thereof wherein the derivative is present in a concentration sufficient to inhibit the effects of activation of the NMDA receptor on neuronal cells. As defined herein, PS derivatives include these modifications to PS alone or in combinations thereof. It further relates to PS derivatives which have modifications at other positions (e.g., C10, C13, C16, C18, C19), alone or in combination, and are inhibitors of NMDA receptor activity. It is reasonable to expect that other PS derivatives such as: PS derivtives in which there are one or more double bonds in rings B, C or D; PS derivatives in which there is deletion of one or more carbon atoms in the A, B, C and/or D rings; and/or PS derivatives in which one or more carbon atoms bridging, for example, C19 and C3, C19 and C5 and/or C19 and C6, is added. The PS derivatives differ from PS in at least one position.

The studies described herein not only reveal another mechanism of non-competitive blockade of the NMDA-induced current, but give a basis for understanding the structural requirements of steroids for NMDA receptor activation. The results described herein demonstrate that particular derivatives or analogues of pregnenolone sulfate represent a novel class of broad spectrum antagonists of excitatory amino acid receptors. These sulfated steroids can be used as anticonvulsant or anti-excitotoxic therapeutic agents.

As further described herein, the effects of steroids on glutamate-mediated synaptic responses have been studied. As described in Example 5, pregnenolone sulfate (PS), which potentiates the NMDA response to exogenously applied NMDA (see U.S. Pat. No. 5,212,167), potentiates spontaneous excitatory post-synaptic currents (EPSCs) in cultures of rat hippocampal neurons. The 5β3αS compound, which inhibits the NMDA response to exogenously applied NMDA, inhibits spontaneous EPSCs in cultures of rat hippocampal neurons. Using whole-cell recording methods, cells were voltage-clamped at −70 mV. Drug solutions were applied to single neurons by pressure ejection from 7-barrel pipets. EPSC potentiation by PS is concentration-dependent, with an $EC_{50}$ of 5.6 μM and maximum potentiation of 198.2%. An analog of PS, 11-keto PS, has no effect on EPSCs, suggesting the effect of PS on EPSCs is specific. When EPSCs mediated by NMDA receptors are blocked with the specific NMDA receptor antagonist APV (40 μM), the potentiation of EPSCs by 100 μM PS is reduced. Conversely, when EPSCs mediated by non-NMDA glutamate receptors are blocked with the specific non-NMDA receptor antagonist DNQX (10 μM), 100 μM PS produces a greater potentiation of EPSCs (453%). These results indicate that PS primarily potentiates EPSCs mediated by NMDA receptors. The effects of PS on EPSCs agree with those of PS on the response induced by exogenously applied NMDA. These observations provide further evidence that neurosteroids such as PS can exert direct neuromodulatory effects on excitatory synaptic transmission in the CNS.

The present invention also relates to a method of modulating or altering (e.g., potentiating; inhibiting) excitatory glutamate-mediated synaptic activity comprising contacting neuronal cells with pregnenolone sulfate or a derivative of pregnenolone sulfate. In one embodiment, the invention relates to a method of potentiating excitatory, glutamate-mediated synaptic activity comprising contacting neuronal cells with pregnenolone sulfate or a derivative of pregnenolone sulfate (e.g., dehydroepiandrosterone sulfate). In another embodiment, the invention relates to a method of inhibiting excitatory glutamate-mediated synaptic activity comprising contacting neuronal cells with a derivative of pregnenolone sulfate (e.g. 5β3αS).

In vivo experiments were also conducted, as described herein, which demonstrate that pregnanolone sulfate derivatives which inhibit NMDA receptor activity (as defined herein), have significant effects for the treatment of diseases associated with excitatory amino acid (e.g., L-glutamate)-induced NMDA receptor activation. The ability to modulate the excitatory glutamate-mediated synaptic activity offers the means for pharmacological intervention in various glutamate-mediated clinical syndromes such as neuropathic pain, drug withdrawal/dependency, epilepsy, glaucoma, chronic neurodegenerative diseases (Parkinson's Disease, Alzheimer's Disease, AIDS, Huntington's Disease), amyotrophic lateral sclerosis, trauma to brain, spinal cord, peripheral ganglia or the enteric nervous system, and anxiety disorders. The compounds described herein can also be used as anti-convulsants, sedative or hypnotic agents or as muscle relaxants. Thus, the present invention also relates to a method of treating a disease associated with L-glutamate-induced NMDA receptor activation selected from the group consisting of: neuropathic pain, drug withdrawal/dependency, epilepsy, glaucoma, chronic neurodegenerative diseases, amyotrophic lateral sclerosis, anxiety disorders, brain cell death, ischaemia, stroke, in a host (e.g., mammal, particularly human) comprising administering to the host an effective amount of a derivative of pregnenolone sulfate. The compounds described herein can also be used as anticonvulsants, sedative or hypnotic agents or as muscle relaxants.

An effective amount of a derivative of pregnenolone sulfate (pregnenolone sulfate derivative) is an amount which produces effective inhibition of the NMDA receptor activity (L-glutamate-induced NMDA receptor activation) when administered to the host. Thus, administration of an effective amount of the pregnenolone sulfate derivative results in amelioration or elimination of the disease state. The amount of pregnenolone sulfate derivative administered to the host will vary depending on a variety of factors, including the pregnenolone sulfate derivative employed, the size, age, body weight, general health, sex, diet of the host, and the time of administration, duration or particular qualities of the disease associated with L-glutamate-induced NMDA receptor activation. For example, the dosage can range from 1 nm to 500 $\mu$M, in particular, 100 nm to 100 $\mu$M and 500 nm to 50 $\mu$M. Adjustment and manipulation of established dose ranges are well within the ability of those skilled in the art.

The pregnenolone sulfate derivative can be administerd to a host in a variety of ways. The routes of administration include intradermal, transdermal, (e.g., slow release polymers), intramuscular, intraperitoneal, intravenous, subcutaneous, oral, epidural, and intranasal routes. Any other convenient route of administration can be used, for example, infusion or bolus injection, or absorption through epithelial or mucocutaneous linings. In addition, continuous or long term (chronic) treatment could be directly through the cerebrospinal fluid using a pump implanted in the subarachnoid space of the brain or spinal cord. Such an implant could contain an external source of steroid or cells engineered to overproduce and secrete sufficient amounts (therapeutic amounts) of the steroid. In addition, the pregnenolone sulfate derivative can be administered together with other compounds of biologically active agents (e.g., pharmaceutically acceptable surfactants, excipients, carriers, diluents and/or vehicles).

In addition, the present invention relates to a method of identifying an agent or compound which modulates glutamate-mediated synaptic activity. For example, neurons are contacted with a steroid described herein which modulates (potentiates or inhibits) excitatory glutamate-mediated synaptic activity and the affinity of the steroid to its receptor (NMDA) is established. The compound to be assessed is added and assessed for its ability to compete with the binding site of the steroid.

The invention is further illustrated in the following examples, which are not intended to be limiting in any way.

EXAMPLE 1

3α-Hydroxy-5β-pregnan-20-one Sulftee (5β3αS) and Androsterone Sulfate Inhibit the NMDA-induced Response Materials and Methods
CELL CULTURES Cultures of dissociated spinal cord neurons were prepared as previously described (Farb, D. H., et al., *J. Cell Biol.*, 80:651–661 (1979)). Briefly, the dissociated cells from 7-day chick embryos were plated on collagen-coated 35-mm tissue culture dishes in Eagle's minimum essential medium supplemented with 2.4 mM glutamine, 10% (v/v) heat-inactivated horse serum, 5% (v/v) chick embryo extract and antibiotics. Cultures were maintained in a humidified atmosphere of 5% $CO_2$, 95% air at 37°. Cytarabine (1 $\mu$M) was added to the culture medium after 36 hr. of the initial plating to inhibit the proliferation of non-neuronal cells. One day later, this medium was replaced with a similar medium supplemented with 20.5 mM glucose, 19 mM KCl, and 2.5% chick embryo extract. Fresh medium was added twice weekly. Cultured neurons were used in experiments within 2–4 weeks after plating.

Electrophysiology

Experiments were carried out in 35-mm tissue culture dishes on the stage of an inverted phase contrast microscope. Whole cell currents were recorded by the whole cell variant of the patch clamp technique (Hamill, O. P., et al., *Pfagers Arch*. 891:85–100 (1981)). Patch electrodes had tip openings of about 2 $\mu$M and resistances of 3–8 M$\Omega$ using an intracellular solution comprised of the following (in mM): 140 CsCl, 11 EGTA, and 10 HEPES (pH adjusted to 7.2 with CsOH). In experiments in which a high concentration of glycine was used, the intracellular solution was replaced with a low chloride (10 mM) pipette solution. This solution contained the following (in mM): 140 potassium gluconate, 10 KCl, 8 sodium gluconate, 11 EGTA, and 10 HEPES (pH adjusted to 7.2 with KOH). To prevent a marked run-down of NMDA-induced current at high NMDA concentrations, 4 mM potassium ATP was included in the intracellular solution. The bath solution contained the following (in mM): 150 NaCl, 4 KCl, 1 $CaCl_2$, and 10 HEPES (pH adjusted to 7.2 with NaOH). No glycine was added to the solutions containing NMDA, because no additional glycine was required to obtain a robust NMDA response, and there was no effect of a maximal concentration (10 $\mu$M) of glycine on 5β3αS inhibition of the NMDA response. All experiments were performed at room temperature (23–25° C.).

Recordings were made using an Axopatch 1B patch clamp apparatus (Axon Instruments, Burlingame, Calif.). Cells with series resistances greater than 10 M$\Omega$ were rejected. After partial compensation, series resistances were between 3.5 and 6 M$\Omega$. The holding potential was maintained at −70 mV unless otherwise noted. Currents were filtered at 1 kHz using an eight-pole Bessel filter (−3 dB) and digitized (40 ms/point) using an on-line data acquisition system (pClamp, Axon Instruments).

Drug solutions were applied to single neurons by pressure ejection (15 psi) from seven-barrel pipettes. Seven-barrel pressure pipettes were positioned approximately 50 $\mu$M from the neuronal soma. Under these conditions, the drug solution in the pressure pipette rapidly and effectively replaces the solution surrounding the target neurons with less than 10% dilution (Choi, D. W., et al., *Nature (Lond.)* 269:342–344 (1977); Chan, C. Y., et al., *Life Sci.*, 83:2061–2069 (1983); Chan, C. Y. and Farb, D. H., *J. Neurosci.*, 5:2365–2373 (1985)). All drugs were obtained from Sigma, with the except of AMPA hydrobromide (Research Biochemicals) and steroids (Steraloids). Stock solutions of steroids were prepared in dimethyl sulfoxide, the final concentration of which was 0.5% (v/v). To obviate the possible effects of dimethyl sulfoxide on the relevant agonist-induced currents, all other drug solutions including NMDA, kainate, AMPA and external buffer (in the pressure pipette) also contained 0.5% dimethyl sulfoxide.

The degree of modulation of the amino acid response by steroid, the percentage change, is expressed as [(I′/I)−1]× 100%, where I is the average of control responses obtained from the same cell before application and after washout of steroid and I′ is the agonist-induced current in the presence of steroid. Throughout, results are expressed as mean±S.E.; statistical comparison of groups was carried out using Student's t test.

Results

Figure 2:
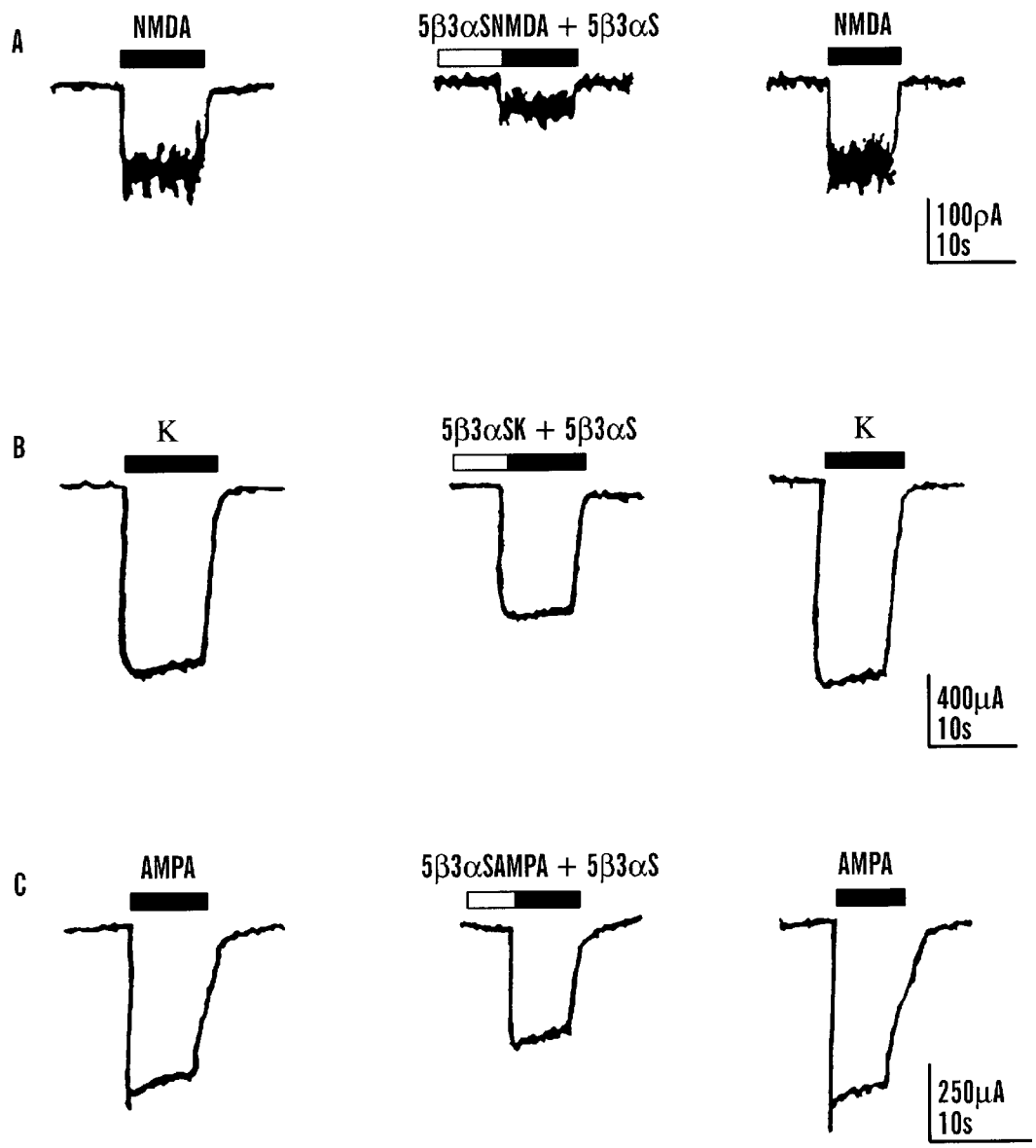
FIG. 2 displays traces of the effects of 100 μM 5β3αS on currents induced by NMDA, kainate and AMPA at holding potentials of −70 mV; the horizontal bar above each trace indicates the period of drug application.

Currents elicited by NMDA, kainate, and AMPA were recorded in primary cultures of chick spinal cord neurons by the whole cell variant of the patch clamp technique. Previously, it has been shown that pregnenolone sulfate potentiates the NMDA-induced whole cell current while inhibiting kainate and AMPA-induced currents (Wu, F. S., et al., *Mol. Pharmacol.* 40:333–336 (1991)). Surprisingly, 5β3αS produced an opposite modulatory effect, inhibiting the NMDA response. The effects of 100 μM 5β3αS on currents induced by NMDA, kainate, and AMPA at holding potentials of −70 mV are illustrated in FIG. 2. The response to 30 μM NMDA was inhibited (66.1±2.7%, n=5) when 5β3αS was applied simultaneously with NMDA. The onset and recovery of inhibition was rapid, and the inhibitory effect of 5β3αS was fully reversible after a wash period of 3–4 min. 100 μM 5β3αS also rapidly and reversibly inhibited 25 μM AMPA-(29.0±3.1%, n=4) and 50 μM kainate- (37.4±4.7%, n=4) induced currents. Application of 5β3αS alone did not produce any direct response.

Results are shown in Table 1 (values are means±S.E.; number of cells is indicated in parentheses). As shown in Table 1, androsterone sulfate, also inhibited the NMDA-induced response. However, not all sulfated steroids inhibit the NMDA response. Dehydroepiandrosterone sulfate (DHEAS) only slightly potentiated the NMDA response (28.8±8.8% potentiation, n=4). Application of 50 μM non-sulfated 5β3α (which represents its maximal solubility in the external buffer) did not produce any significant effect on the 30 μM NMDA-induced current (3.6±8.4% potentiation, n=4), indicating that the sulfate moiety is important for the effect of 5β3αS on the NMDA response.

Figure 3:
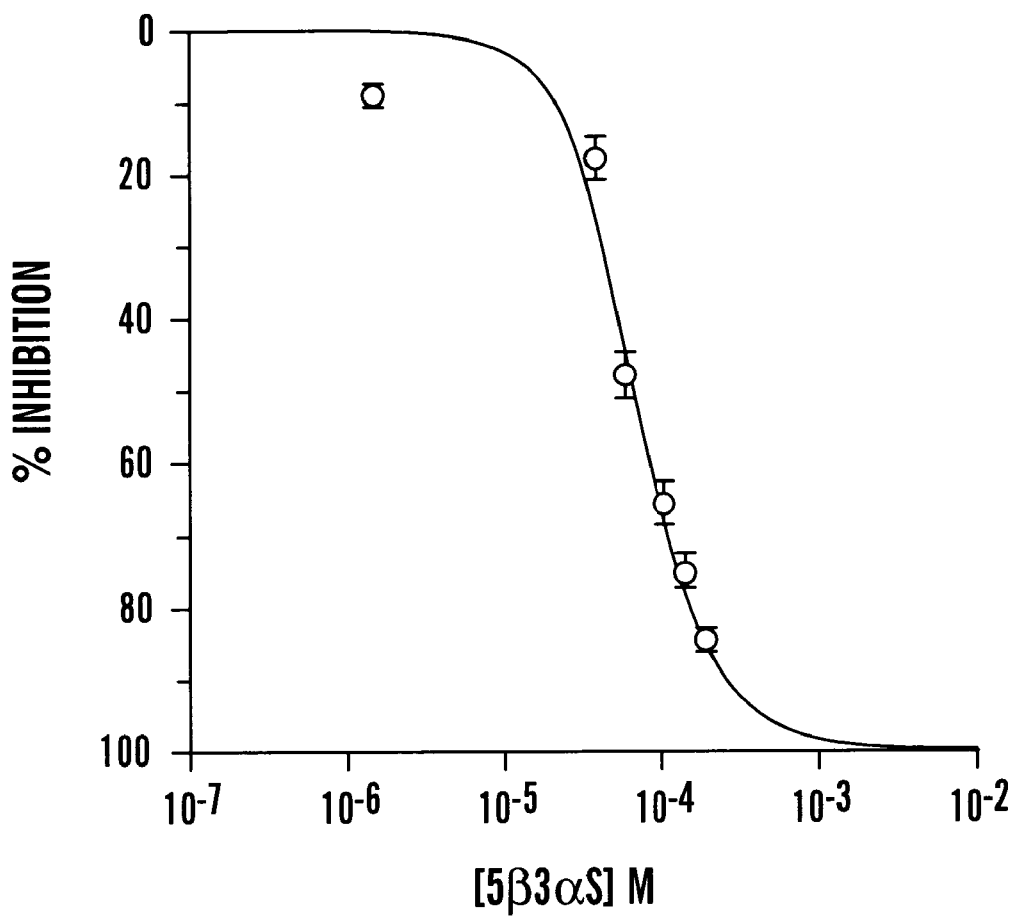
FIG. 3 is a graph of molar concentration of 5β3αS versus % inhibition indicating the concentration-response curve for inhibition of NMDA response by 5β3αS (mean of four to eight experiments).

To quantitatively evaluate the potency and efficacy of 5β3αS for NMDA receptors, pooled data were used to construct the concentration-response curve for inhibition of the 30 μM NMDA response by 5β3αS. As shown in FIG. 3, 5β3αS produced a concentration-dependent blockade of the current induced by 30 μM NMDA, and curve-fit analysis revealed an $EC_{50}$ of 62.1 μM and maximal inhibition of 101.1%.

To investigate the mechanism of inhibition by 5β3αS, pooled data were used to construct a concentration-response curve for NMDA in the presence and absence of 50 μM 5β3αS. To obviate cell-to-cell variability with respect to the maximal current induced by NMDA, all responses were normalized to the peak current induced by 100 μM NMDA. 5β3αS markedly reduced the NMDA maximal response with little effect on the NMDA $EC_{50}$. (In the absence of 5β3αS, $EC_{50}$=155.6 μM, $I_{max}$=2.56, and $n_H$=1.01). In the presence of 5β3αS, $EC_{50}$=105.7 μM, $I_{max}$=1.10, and $n_H$=1.46) NMDA $EC_{50}$ values are close to the $EC_{50}$ reported for cultured chick motor neurons (O'Brien, R. J. and Fishbach, G. D., *J. Neurosci.*, 6:3257–3283 (1986)). This result suggests that the action of 5β3αS on the NMDA response is noncompetitive in nature and that 5β3αS acts through a site distinct from the NMDA recognition site.

Because the noncompetitive NMDA antagonists such as MK-801 act on the ion channel in a use-and voltage-dependent manner (Hucttner, J. E. and Bean, B. P., *Proc. Natl. Acad. Sci. USA*, 85:1307–1311 (1988)), the voltage dependence of the effect of 5β3αS on the NMDA-induced current was tested. The average inhibition produced by 100 μM 5β3αS at +50 mV (62.0±2.8%, n=5) was not significantly different from that at −70 mV (63.2±2.7%, n=5) (p>0.05, paired t test). This result indicates that the blockade by 5β3αS of the NMDA response is voltage independent. Use dependence was not observed on the time scale of these experiments; the first application of 5β3αS in the presence of NMDA elicited an immediate blockade of both peak and plateau responses, and the recovery of the NMDA response after washout of 5β3αS was rapid.

The response of the NMDA receptor is positively modulated by glycine, and glycine may be an absolute requirement for receptor function (Johnson, J. W. and Ascher, P., *Nature (Lond.)* 325:529–531 (1987)). Some inhibitors of the NMDA response, such as 7-chlorokynurenic acid, act by blocking the glycine site of the NMDA receptor (Wong, E. H. F. and Kemp, J. A., *Annu. Rev. Pharmacol. Toxicol.*, 81:401–525 (1991)). To determine whether 5β3αS acts as a competitive antagonist at the glycine recognition site, the effect of 5β3αS on the NMDA responses in the presence of a saturating concentration (10 μM) of glycine was examined. 50 μM 5β3αS still reduced the current induced by 30 μM NMDA with added glycine. Moreover, the average inhibition by 5β3αS (51.3±3.5%, n=4) was not significantly different from that in the absence of glycine (49.1±3.4%, n=4) (p>0.5, unpaired t test). This result is consistent with the view that the effect of 5β3αS on the NMDA-induced current is not mediated by the glycine recognition site.

Discussion

The highly lipophilic nature of the steroids and the evidence that phospholipids are capable of binding steroids with high specificity (Majewska, M. D., *Biochem. Pharmacol.* 35:3781–3788 (1987)) raise the possibility that the effect of 5β3αS is mediated by interactions with the membrane lipids surrounding the NMDA receptor protein. However, we have shown that another pregnenolone sulfate analogue, DHEAS, has only a slight effect (28.8% potentiation) on the NMDA response in comparison with the effect of pregnenolone sulfate, which potentiates the NMDA response by 197% (Wu, F. S., et al., *Mol. Pharmacol.* 40:333–336 (1991)). This finding argues that antagonism of the NMDA-induced current by 5β3αS is a specific effect.

There are a number of potential sites at which 5β3αS could exert its blocking action, including: 1) competitive inhibition at the NMDA binding site, 2) blockade of the NMDA receptor associated channel, or 3) noncompetitive inhibition or allosteric modulation at a distinct site.

First, competition of 5β3αS for the NMDA binding site cannot account for the observed result. The results show that the antagonism by 5β3αS of the NMDA-induced current is not attenuated by increasing concentrations of NMDA.

Second, blockage of a cation channel by a negatively charged molecule such as 5β3αS seems unlikely on theoretical grounds. The cloned NMDA receptor has a putative second transmembrane domain which is thought to be involved in lining the ion channel and is flanked by negatively charged amino acid residues (Moriyoshi, K., et al., *Nature* 354:31–37 (1991)). This would deter entry of a sulfated molecule into the channel. The lack of voltage and use dependent also suggests that the interaction of this compound with the inner channel wall is unlikely.

The NMDA receptor is known to have a glycine recognition site (Johnson, J. W. and Ascher, P., *Nature (Lond.)* 325:529–531 (1987)) in addition to the agonist binding site. The inhibitory action of 5β3αS on the NMDA-induced currents cannot be surmounted by a saturating concentration of glycine. This experiment suggests that the steroid and glycine do not act at a common site.

Previously it has been shown that pregnenolone sulfate acts as a positive allosteric modulator at the NMDA receptor. Surprisingly, slight modifications of pregnenolone sulfate structure (reducing the C-5 position double bond, 3β-hydroxy to 3α-hydroxy) change the modulation of the NMDA receptor mediated response from a positive to a negative direction. Interestingly, 5β3αS produces opposite effects to pregnenolone sulfate only at the NMDA response. It elicits inhibitory effects similar to those of pregnenolone sulfate at the AMPA and kainate response. This result provides evidence that the structural requirements for modulation of NMDA and non-NMDA receptors by steroids are different. The ineffectiveness of non-sulfated 5β3α on the NMDA response demonstrates that sulfation converts an inactive steroid to an active steroid inhibitor, suggesting that steroid sulfotransferase could be an important enzyme in regulating NMDA receptor activity in the CNS.

The studies described herein not only reveal another mechanism of non-competitive blockade of the NMDA-induced current, but give a basis for understanding the structural requirements of steroids for NMDA receptor activation. The results described herein demonstrate that particular derivatives or analogues of pregnenolone sulfate represent a novel class of broad spectrum antagonists of excitatory amino acid receptors. The sulfated steroids can be used as anticonvulsant or anti-excitotoxic therapeutic agents.

TABLE 1

Effects of Steroids On the 30 μM NMDA-Induced Response

| Steroid | Change of response (%) |
|---|---|
| 5β3αS (100 μM) | −66.1 ± 2.7 (5) |
| 5β3α(10 μM) | −3.4 ± 3.5 (4) |
| (50 μM) | +3.6 ± 3.4 (4) |
| Androsterone sulfate (100 μM) | −18.1 ± 2.6 (3) |
| DHEAS (100 μM) | +28.8 ± 8.6 (4) |
| β-Estradiol benzoate (20 μM) | +24.3 ± 18 (3) |

EXAMPLE 2

Epipregnanolone Sulfate (3β-Hydroxy-5β-pregnan-one Sulfate; 5β3βS) Inhibits NMDA Receptor Activity at a Specific Site of Action Experiments were conducted as described in Example 1 to determine the ability 5β3βS to inhibit NMDA, kainate and AMPA responses.

Application of 100 μM 5β3βS rapidly and reversibly inhibited responses to 30 μM NMDA by 59%, 50 μM kainate by 33% and 25 μM AMPA by 43%. 5β3βS alone at high concentrations (greater than or equal to 100 μM) often induced a small outward current. This current was not observed in the CsCl-containing intracellular solution, indicating that it is a K$^+$ current. Moreover, in the CsCl-containing solution, 5β3βS (100 μM) still inhibited the NMDA response. In 2 cells, the average inhibition produced by 5β3βS was 49±5.0%, which was not significantly different from that measured in the KCl-containing intracellular solution (p>0.05, unpaired t test). This makes it unlikely that the 5β3βS-induced outward current could account for the inhibition of the NMDA response.

A stereoisomer of 5β3βS, 5α-pregnan-3β-ol-20-one sulfate (5α3βS) failed to inhibit (1±2.6%, n=6) the NMDA-induced current, suggesting that the interaction of 5β3βS with the NMDA receptor is stereospecific about carbon-5, but not at carbon-3. This stereoselectivity of action makes it unlikely that 5β3βS inhibits the NMDA receptor through a nonspecific mechanism, such as perturbation of the lipid bilayer proposed for short-chain alcohols (Lovinger et al., *Science*, 243:1721–1724 (1989), but supports instead the existence of a specific site of action.

To determine whether block of the NMDA response by 5β3βS is voltage-dependent, the effect of 100 μM 5β3βS on the current induced by 30 μM NMDA at two different holding potentials was examined. In 2 cells, the average inhibition produced by the 5β3βS is similar at −70 mV and +50 mV, indicating that the effect of 5β3βS on the NMDA response is not voltage-dependent. In addition, both block of the NMDA response and recovery from blockade by 5β3βS are rapid, suggesting that 5β3βS inhibition of the NMDA response is not agonist-dependent. Thus, the voltage-independent action of 5β3βS virtually excludes an interaction with the phencyclidine or Mg$^{2+}$ binding sites of the NMDA receptor.

To determine whether inhibition by 5β3βS of the NMDA response is mediated via the glycine recognition site, the effect of 5β3βS (100 μM) on the current induced by 30 μM NMDA in the presence of a saturating concentration (10 μM) of glycine was investigated. Inhibition of the NMDA response by 5β3βS did not significantly differ from that measured without added glycine (p>0.05, unpaired t test), indicating that the 5β3βS site is distinct from the glycine recognition site.

Further experiments were conducted to demonstrate whether sulfate (PS) and 5β3βS acted through a common regulatory site as described below.

Intracellular Steroids do not Alter Modulation of the NMDA Response by Extracellularly Applied Steroids In order to test whether the potentiation by PS is mediated by an intracellular site of the NMDA receptor, whole-cell current measurement was performed in the presence of intracellular 100 μM PS. When PS was applied intracellularly by inclusion in the electrode buffer, the average NMDA response did not differ significantly from control and remained stable throughout the recording period (3–5 min.). This result suggested that intracellular PS can not obtain access to the steroid modulatory site of the NMDA. To confirm this result, the NMDA response was normalized to the cell capacitance (pF) to obviate cell-to-cell variability with respect to the size of the cell. No significant differences in normalized currents were observed in the presence or absence of PS, suggesting that PS does not act at an intracellular site on or associated with the NMDA receptor. In addition, the average potentiation of the NMDA response by extracellularly applied PS in the presence of intracellular PS (152±23%, n=4) was not significantly different from that in the absence of intracellular PS (158±24%, n=4). Both block the NMDA response, and recovery from blockade by extracellular 5β3βS is rapid, with no obvious use-dependence, such as is seen with MK-801 and PCP (Halliwell, R. F., et al., *Br. J. Pharmacol.*, 96:480–494 (1989); Lerma, J. et al., *Neurosci. Lett.*, 123:187–189 (1991)). Similarly, the addition of 200 μM 5β3βS to the intracellular buffer does not inhibit the NMDA-induced currents. Furthermore, the inhibitory effect of extracellular 100 μM 5β3βS does not significantly differ in the presence of intracellular 5β3βS (44±4%, n=4) from that in the absence of intracellular 5β3βS (48±4%, n=4).

Bidirectional Modulation of the NMDA-R by Steroids is not Mediated by the Polyamine Site In agreement with previous reports (Sprosen, T. S., et al., *Eur. J. Pharmacol.*, 179:477–478 (1990); Williams, K. et al., *Neuron*, 5:199–208 (1990)), spermine (10–250 μM) potentiates the NMDA induced current. Potentiation is maximal (136±33%, n=4) at a spermine concentration of 100 μM. When the concentration of spermine is further increased to 250 μM, spermine is less effective in potentiating the NMDA response (67±21%, n=3). To determine whether PS and spermine act through a common regulatory site on the NMDAR, the effect of PS (100 μM) on the NMDA response in the presence of a maximally potentiating concentration (100 μM) of spermine was examined. In the absence of spermine, PS (100 μM) potentiated the response to 30 μM NMDA by 150±14% (n=14). In the presence of 100 μM spermine, PS potentiated the NMDA response by 178±12% (n=6), which was not significantly different from PS potentiation in the absence of spermine. These results suggested that potentiation of the NMDA response by PS is mediated by a site distinct from that responsible for potentiation by spermine. Similarly, 100 μM 5β3βS inhibited the NMDA response by 50±5% (n=5) in the presence of 100 μM spermine, which was not significantly different from the percentage of inhibition in the absence of spermine. Because this concentration of 5β3βS is close to its $EC_{50}$, the percentage of inhibition by 5β3βS should be reduced if 5β3βS and spermine compete for a common site. Therefore, the inhibitory steroid modulatory site is distinct from the spermine modulatory site.

Bidirectional Modulation of the NMDA-R by Steroids is not Mediated by the Arachidonic Acid Site Arachidonic acid has been shown to potentiate the NMDA response by directly acting at the NMDA receptor (Miller, B. et al., *Nature*, 355:722–725 (1992)). Because PS has amphiphilic properties similar to arachidonic acid, whether PS and arachidonic acid act through the same site was examined. A maximal concentration of arachidonic acid (10 μM) alone potentiated the 30 μM NMDA response by 120±35% (n=5), while in the presence of 100 μM PS, arachidonic acid potentiated the NMDA response by 158±22% (n=4). Conversely, 100 μM PS potentiated the NMDA response by 182±25% (n=4) in the presence of 10 μM arachidonic acid, which did not differ significantly from potentiation in the absence of arachidonic acid. It is therefore likely that PS and arachidonic acid potentiate the NMDAR through independent mechanisms. Similarly, arachidonic acid did not affect the percentage of inhibition of 5β3βS (49±5%, n=5), indicating that the inhibitory steroid site is also distinct from the arachidonic acid modulatory site.

Bidirectional Modulation of the NMDA Response by Steroids is not Mediated by the Redox Site In the presence of 4 mM dithiothreitol (DTT), there is a gradual "run-up" of the NMDA response, with the NMDA current increasing to 273±19% (n=6) of control after 180 seconds of DTT exposure. To examine whether PS interacts with the redox modulatory site of the NMDA receptor, potentiation of the NMDA response by PS was measured after prolonged exposure to DTT. After approximately an hour of exposure to 4 mM DTT (in the bath solution), the mean NMDA induced current was significantly increased (326±82 pA; n=13), compared to control cultures (121±16 pA; n=25). However, there was no significant change in potentiation of the NMDA induced current by 100 μM PS (165±26%, n=4). Similarly, PS potentiation of the NMDA response was not significantly changed (161±12%, n=4) after approximately 1 hour of exposure to 10 mM DTT. As an additional test, cells were treated with the sulfhydryl alkylating agent N-ethylmaleimide (NEM) to alkylate the sites responsible for the redox modulation of the NMDA receptor. Cultures were treated for 5 min. with 4 mM DTT, followed by a 2 min. treatment with 4 mM DTT plus 300 μM N-ethylmaleimide (NEM). Cultures were then washed 4 times and potentiation of the 30 μM NMDA response by PS was measured. The mean NMDA induced current was significantly increased (367±82 pA, n=25), compared to control cultures (121±16 pA, n=25), but potentiation of the NMDA response by PS was not significantly (p>0.1) reduced (103±23%, n=4). Inhibition of the NMDA response by 5β3βS was also unchanged after NEM treatment (53±5% inhibition, n=4).

5β3βS and PS ACT THROUGH DISTINCT SITES

To investigate whether the structurally similar compounds 5β3βS and PS act through the same site to modulate the NMDA response, the effects of 5β3βS and PS in combination were examined. In the presence of 200 μM PS, 200 μM 5β3βS inhibited the peak NMDA response by 50±4% (n=4), which was not significantly different from the inhibition of 59±3% (n=4) measured in the absence of PS. Conversely, potentiation of the NMDA response by 100 μM PS was still evident in the presence of 200 μM 5β3βS. Moreover, the $IC_{50}$ for inhibition of the NMDA response by 5β3βS was similar in the presence and absence of 200 μM PS 120 μM and 143 μM, respectively.) Taking the PS $EC_{50}$ of 57 μM for potentiation of the NMDA response (Wu, F.-S. et al., *Mol. Pharmacol.*, 40:333–336 (1991)) as an approximation of its $K_d$, competitive inhibition would predict that the $IC_{50}$ for 5β3βS measured in the presence of PS would be increased by a factor of 4.5. These results indicate that 5β3βS inhibits the NMDA response via a site distinct from the PS modulatory site.

Modulation of the NMDA Response by Steroids in Oocytes Expressing Recombinant NMDA Receptors The recent cloning of cDNAs encoding NMDA receptor subunits has greatly facilitated the study of the functional modulation of the NMDA receptor. It has been shown the coexpression of the NR1 subunit (Moriyoshi, K., et al., *Nature*, 354:31–37 (1991)) with one of four NR2 subunits (NR2A–NR2D) (Monyer, H., et al., *Science*, 256:1217–1221 (1992); Ishii, T., et al., *J. Biol. Chem.*, 268:2836–2843 (1993)) produces functional channels that exhibit many of the pharmacological properties of native NMDA receptors. Recent studies suggest that these recombinant heterometric channels display different sensitivities to the NMDA receptor modulators depending on which of the four NR2 subunits assembles with NR1 (Monyer, H. et al., *Science*, 256:1217–1222 (1992); Kusuwade, T., et al., *Nature*, 358:36–41 (1992); Laurie, D. J., et al., *Eur. J. Pharmacol.*, 268:335–345 (1994); Masood, K., et al., *Mol. Pharmacol.*, 45:324–329 (1994)).

Oocyte Electrophysiology

RNA preparation. mRNA were prepared through in vitro transcription of $NR1_{100}$ and NR2A cDNAs using the mMessage mMachine kit (Ambion, Tex.). $NR1_{100}$ and NR2A clones were kindly provided by Dr. Zukin and Dr. Nakanishie.

Xenopus expression system. Female, oocyte positive *Xenopus laevis* frogs were purchased from Nasco, Inc. (WI). The frogs were kept on a 12/12 light-dark cycle and maintained on a diet of chopped calf liver every 3 days. Prior to surgery, frogs were anesthetized in a 0.15% Tricaine solution (Sigma, Mo.) for 30–45 minutes. Ovarian sections containing the follicular oocytes were removed through a lateral abdominal incision and were immediately placed in calcium-free ND96 solution (in mM):96 NaCl; 1 $MgCl_2$; 2 KCl; 5 Hepes; 2.5 pyruvate (pH adjusted to 7.4 with NaOH). Following a 2 hr. incubation in 0.2% collagenase type II (Sigma, Mo.) at room temperature, individual defolliculated oocytes were transferred into 60×15 mm glass petri dishes containing ND96 solution (in mM): 96 NaCl; 1 $MgCl_2$; 2 KCl; 1.8 $CaCl_2$; 5 Hepes; 2.5 pyruvate (pH adjusted to 7.4 with NaOH). The isolated oocytes were maintained in an incubator at 18° C. On the following date, batches of 20–40 selected oocytes (Dumont stage V and VI) were injected with 50 nl of prepared RNA solution (0.5 ng of NR1 and 12 ng of NR2A mRNAs per oocyte) using an electronic microinjector (Drummond, Pa.). The injected oocytes were used for electrophysiological experiments following 4–10 day incubation at 18° C.

Electrical recording and drug application. The ion current recordings were obtained in two electrodes voltage-clamp mode using an Axoclamp-2A amplifier (Axon Instruments, Inc., CA). The microelectrodes were fabricated with a programmed puller (Sutter Instrument Co., CA) from glass capillaries (Dagan, Minn.) and filled with 3M KCl solution. The resistance of filled microelectrodes was in the range of 2.5–3.5 MΩ. The oocytes were clamped at a holding potential of –70 mV. The membrane current was filtered at 500 Hz and sampled at 100 Hz frequency. The drugs were applied using a gravity driven external perfusion system. The data acquisition and external perfusion control were done using SuperScopeII software package (GW Instruments, MA). All experiments were performed at room temperature of 22–24° C.

The degree of modulation of the amino acid response by steroids, the percent change, was defined at (I'/I–1)×100%, where I and I' are respectively the agonist-induced currents in the absence and presence of steroid. Throughout, results are expressed as mean±SEM; statistical comparison of groups was carried out using Student's t test.

In order to investigate whether PS and 5β3βS act upon different receptor populations, modulatory effects of steroids were assessed using oocytes expressing only $NMDAR1_{100}$ and NMDAR 2A subunits. NMDA dose response curves yielded $EC_{50}$ and Hill coefficient of 62±4 μM and 1.5±0.1, respectively (n=4). Like 5β3αS (Park-Chung, M., et al., *Mol. Pharmacol.*, 46:462–465 (1994)), 5β3βS decreased the maximal NMDA response, but produced only a slight shift in the NMDA $EC_{50}$ (48±4 μM; n=4), suggesting that the inhibition of the NMDA response by 5β3βS was noncompetitive. 200 μM 5β3βS inhibited (54±8%, n=4) and 100 μM PS potentiated (292±34%, n=8) a near maximal NMDA response (200 μM). To examine whether 5β3βS and PS acted through a single site to modulate the NMDA response, the effect of 5β3βS in the presence of a maximal concentration of PS was assessed. The inhibition of the peak NMDA response by 200 μM 5β3βS in the presence of 200 μM PS (54±5%; n=5) was not significantly different from that measured in the absence of PS (46±8%; n=4). Moreover, there was no significant change in the $IC_{50}$ for 5β3βS in the presence and absence of 200 μM PS (124 μM and 151 μM, respectively). Again, these results were consistent with the view that 5β3βS inhibited the NMDA response via a site distinct from the PS modulatory site.

Furthermore, as with neurons, 5β3αS had an inhibitory effect on NMDA responses of $NR1_{100}$/NR2A injected oocytes, and the interaction between PS and 5β3αS was not competitive, indicating that these two steroids act through distinct sites.

Discussion

SITES FOR ACTION OF STEROIDS

The NMDA response can be blocked in a voltage-dependent manner by noncompetitive antagonists of the NMDAR including $Mg^{2+}$ (Nowak, L., et al., *Nature (Lond.)*, 307:462–465 (1984)), MK-801, and phencyclidine (Honey, C. R., *NeuroSci. Lett.*, 61:135–139 (1985)), which are thought to bind at sites within the channel. In contrast, inhibition by 5β3βS is not voltage dependent. As 5β3βS is charged, voltage dependent inhibition would be expected if access of 5β3βS to its binding site required entry into the channel. Moreover, there is no evidence of use-dependent inhibition because peak inward currents evoked by repeated applications of NMDA in the presence of 5β3βS do not progressively decline. The absence of voltage- or use-dependence argues that inhibition by 5β3βS is not mediated by the $Mg^{2+}$ or MK-801 binding sites.

Previous reports suggest that PS might be able to diffuse within or across the membrane to access any potential site of action (Wong, M. et al., *J. Neuroscience*, 12:3217–3225 (1992); Bowlby, M., *Mol. Pharmacol.*, 43:813–819 (1993)). However, any significant changes in the average amplitude of the NMDA response with intracellular steroids was not observed. In addition, there was no gradual increase or decrease in the NMDA responses with time (~5 min.), suggesting that intracellular steroids do not modulate the NMDA response even in a slow time scale. Furthermore, the potentiation by PS or inhibition by 5β3βS, when applied extracellularly, is not altered in the presence of intracellular steroids. These results argue that the sites of action of PS and 5β3βS are associated with the extracellular side of the membrane. In a previous report, extracellularly applied PS potentiated NMDA responses in an on-cell patch that was not directly exposed to PS (Bowlby, M., *Mol. Pharmacol.*, 43:813–819 (1993)). In view of the present results, this finding might be explained if PS is able to reach its site of action by lateral diffusion within the plane of the membrane.

It has been shown that potentiation of the NMDA response by PS and inhibition by 5β3αS is not mediated by the glycine modulatory site (Wu, F.-S., et al., *Mol. Pharm.*, 37:597–602 (1991); Bowlby, M., *Mol. Pharmacol.*, 43:813–819 (1992); Park-Chung, M., et al., *Mol. Pharmacol.*, 46:146–150 (1994)). Similarly, the percentage of inhibition of the NMDA response by 5β3βS is not reduced in the presence of a saturating concentration of glycine, indicating that the inhibition is not due to competition with endogenous glycine for the glycine modulatory site.

A variety of other modulatory sites associated with the NMDAR have been proposed, including sites for polyamines, arachidonic acid, and redox agents. Polyamines such as spermine or spermidine at micromolar concentrations have been shown to increase the NMDA response, and their site of action is distinct from the glycine site (Ransom, R. W., et al., *J. Neurochem.*, 51:830–836 (1988); Williams, K., et al., *Mol. Pharmacol.*, 36:575–581 (1989); Sprosen, T. S., et al., *Eur. J. Pharmacol.*, 179:477–478 (1990); Williams, K. et al., *Neuron*, 5:199–208 (1989)). Another NMDA receptor modulator, arachidonic acid, has amphiphilic properties similar to PS, and it has been proposed that the site for action of arachidonic acid is the putative fatty acid binding domain of the NMDA receptor (Petrou, S., et al., *Trends*

Biol. Sci., 18:12–13 (1993)). In addition, reduction of the channel's redox modulatory site(s) has been shown to enhance the NMDA-induced currents, while oxidation produces the opposite effect (Aizenman, E., et al., Neuron, 2:1257–1263 (1989)). Thus, whether positive or negative modulation of the NMDAR by steroids is mediated by any of these known modulatory sites was investigated. Both potentiation of the NMDA response by PS and inhibition by 5β3βS persist in the presence of high concentrations of spermine or arachidonic acid, arguing that the modulatory effects of these steroids are not mediated by either the polyamine or arachidonic acid sites. Similarly, potentiation by PS and inhibition by 5β3βS persist following prolonged incubation with DTT or after alkylation with NEM, suggesting that steroids do not interact with redox modulatory sites. Taken together, these results provide strong support for the existence of a novel extracellular steroid modulatory site(s).

The Interaction Between PS and 5β3βS

Surprisingly, the interaction between PS and 5β3βS is not competitive, arguing that these steroids produce their respective positive and negative modulatory effects by acting through different sites. This conclusion is based on the following observations: (i) Inhibition of the NMDA response by 5β3βS does not change with the addition of a near maximal concentration of PS; (ii) Potentiation by PS of the NMDA response is still evident in the presence of a high concentration of 5β3βS; and (iii) There is no significant change in the $IC_{500}$ for 5β3βS in the presence of PS. It does not seem likely that PS and 5β3βS act upon different populations of NMDARs, as it is possible to achieve nearly complete inhibition of the NMDA response at high concentrations of 5β3βS, arguing against the existence of a population of receptors resistant to 5β3βS but sensitive to PS. In addition, bidirectional modulation of the NMDA response by PS and 5β3βS was observed in oocytes expressing only $NMDAR1_{100}$ and NMDAR2A subunits and as with neuronal NMDA receptors, the interaction between these two modulators was not competitive. Thus, there must be at least two distinct steroid modulatory sites with the capacity to modulate NMDAR function.

Physiological and Pharmacological Significance

Recently, it has been demonstrated that intracerebroventricular injection of PS enhances memory retention (Flood, J. F., et al., Proc. Nat'l. Acad. Sci., 89:1567–1571 (1992)). PS also has been shown to be effective in blocking NMDA receptor antagonist-induced deficits in a passive avoidance memory task (Mathis, C., et al., Psycopharmacol., 116:201–206 (1994)) and antagonizing dizocilpine-induced amnesia in rats (Cheney, D. L., et al. (1995)).

The inhibitory sulfated steroids such as 5β3βS or 5β3αS are useful for preventing excitotoxic neuronal death. It has been shown that there is an increased release of NMDA receptor modulators such as glycine (Globus, M., et al., Neurosci. Lett., 127:39–42 (1991)) or arachidonic acid (Rehncrona, S., et al., J. Neurochem., 38:84–93 (1982)) in ischaemia. Increased concentrations of glutamate and endogenous modulators of NMDA receptor are expected to potentiate NMDA receptor currents and exacervate glutamate-mediated excitotoxicity. Because 5β3βS can inhibit the NMDA response in the presence of glycine, polyamine or arachidonic acid, it can effectively inhibit excessive NMDA receptor activation during pathophysiological conditions such as stroke, ischemia, and hypoxia neuronal damage.

As described herein, sulfated steroids PS and 5β3βS act at unique sites of the NMDA receptor and they exert their positive and negative modulation through independent pathway. These results support the view that these sulfated steroids constitute a novel class of functional modulators of the NMDA receptor.

EXAMPLE 3

Figure 4:
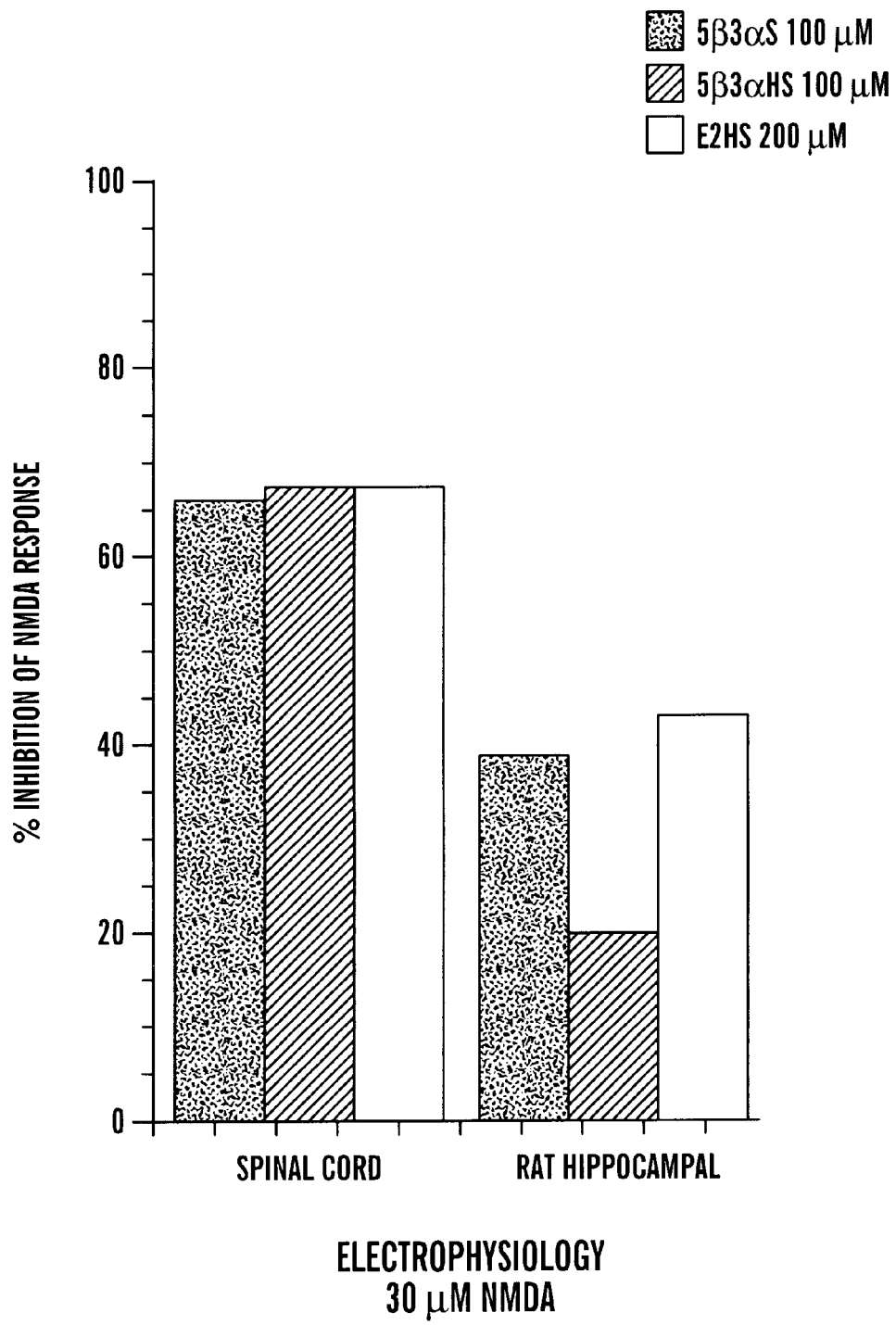
FIG. 4 is a bar graph of % inhibition of the NMDA response as measured by electrophysiology, demonstrating that 5β3αS, 5β3α hemisuccinate and 17β-estradiol hemisuccinate inhibit the NMDA response.

Additional Derivatives of Pregnenolone Sulfate which Inhibit NMDA Receptor Activity The electrophysiology of additional pregnenolone derivatives were analyzed as described in Example 1. The results of the following compounds: 5β3αS, 5β3α hemisuccinate, 17β-estradiol hemisuccinate, 11β-OH-pregnenolone sulfate, 5β3βS and 5α3αS are summarized in Table 2. FIG. 4 is a bar graph of electrophysiology versus % inhibition of the NMDA response demonstrating that 5β3αS, 5β3α hemisuccinate and 17β-estradiol hemisuccinate inhibit the NMDA response.

As shown in FIG. 4, the % inhibition of NMDA response in rat hippocampal cells by 5β3α hemisuccinate was approximately 20%. In 2 of the 6 experiments conducted using 5β3α hemisuccinate, the compound was ineffective. However, in 4 of the 6 experiments the % inhibition of NMDA response in rat hippocampal cells was much larger. The results from all 6 experiments were averaged into the final result, which produced the lower % inhibition overall.

TABLE 2

Effects of Steroids On the NMDA Response

| Steroid | μM (Steroid) | % Change of response (30 μM NMDA-Induced Current or NMDA Response) | |
|---|---|---|---|
| | | chick spinal cord neurons | rat hippocampal neurons |
| 5β3αS | 100 | −66 ± 2.7 (5 cells) | −36.5 ± 2.1 (5 cells) |
| 5β3α hemisuccinate | 100 | −67 ± 2.0 (2 cells) | −18.0 ± 8.0 (6 cells) |
| 17β-estradiol hemisuccinate | 200 | −67 ± 9.5 (3 cells) | −41 ± 7.0 (4 cells) |
| 11β-OH-pregnenolone sulfate | 100 | −31 ± 2 (3 cells) | |
| 5β3βS | 100 | −59 ± 3 (4 cells) | |
| androsterone sulfate | 100 | −18 ± 2.6 (3 cells) | |

EXAMPLE 4

Inhibitors of NMDA Receptor Activity Also Protect Against Excitotoxicity

Trypan blue exclusion was used to evaluate the ability of derivatives of pregnenolone sulfate to inhibit NMDA-induced cell death in primary neuronal cultures of rat hippocampal formation.

Mixed neuronal and glial cultures of hippocampal tissue were derived from fetal rats on day 18 of embryonic development and were maintained in culture for 16 to 24 days (Brewer, G. J., Brain Res., 494: 65–74 (1989)). Care for the animals used in this study was in accordance with institutional guidelines. Hippocampal tissue from Sprague-Dawley rat pups was collected immediately following removal from dams sacrificed with $CO_2$ on embryonic day 18. Cells were dissociated by trituration in $Ca^{2+}/Mg^{2+}$ free Hank's basic salt solution supplemented with 4.2 mM bicarbonate, 1 mM sodium pyruvate, 20 mM HEPES, 3 mg/ml BSA, and pelleted by centrifugation (900 rpm, 3 min). The resulting pellet was suspended in DMEM supplemented with 2.4 mg/ml BSA, 26.5 mM sodium bicarbonate, 1 mM sodium pyruvate, 20 mM HEPES, 10% FBS, 100 units/ml penicillin, 100 μg/ml streptomycin, and a modification of Brewers B16 defined components (with 250 mM vitamin B12 and without catalase, glutathione, and superoxide dismutase) (Pike, C. J., et al., *Neurosci.* 13:1676–87 (1993)) and plated onto poly-L-lysine coated 24 well culture dishes (Nunclon) at a density of 15,000 cells/cm$^2$ and were maintained in a humidified incubator in 5% $CO_2$/95% air at 37° C. After 5 days in vitro, nonneuronal cell division was inhibited by exposure to $2\times10^{-6}$ M cytosine arabinoside for 48 hrs. Cells were subsequently maintained in medium identical to that used for platting without BSA or FBS.

The number of living neurons was determined by assessing the ability of cells to exclude trypan blue 16 hrs. after the addition of drug solutions to the medium of individual culture wells (Dawson, V. L., et al., *Proc. Natl. Acad. Sci. USA*, 88:6368–6371 (1991)). Drugs were introduced to cultures in 100 μl of conditioned media, collected from experimental cultures just prior to treatment, to a final volume of 0.5 ml. NMDA was dissolved in DMEM at concentrations of 0–5 mM so that addition of 10 μl yielded final concentrations of 0–100 μM. MK-801, a positive control, was dissolved in DMEM at a concentration of 1 mM so that addition of 5 μl yielded a final concentration of 10 μM. Control cultures were exposed only to an equivalent volume of DMEM, and concentration of DMSO (0.5%). The concentrations of the pregnenolone sulfate derivatives were as follows: 10–100 μM 5β3αS, 100 μM 5β3α hemisuccinate and 200 μM 17β-estradiol hemisuccinate.

After exposure to drugs, the medium was replaced by 0.1 M sodium phosphate buffer/0.4% trypan blue. Cell death was assessed by counting the number of trypan blue positive and negative neurons in five high power fields per culture well with an inverted phase contrast microscope using both bright field and phase settings. Cell death is expressed as the ratio of the number of trypan blue positive to total number of cells counted in each well×100 (percent cell death).

Results

Figure 5:
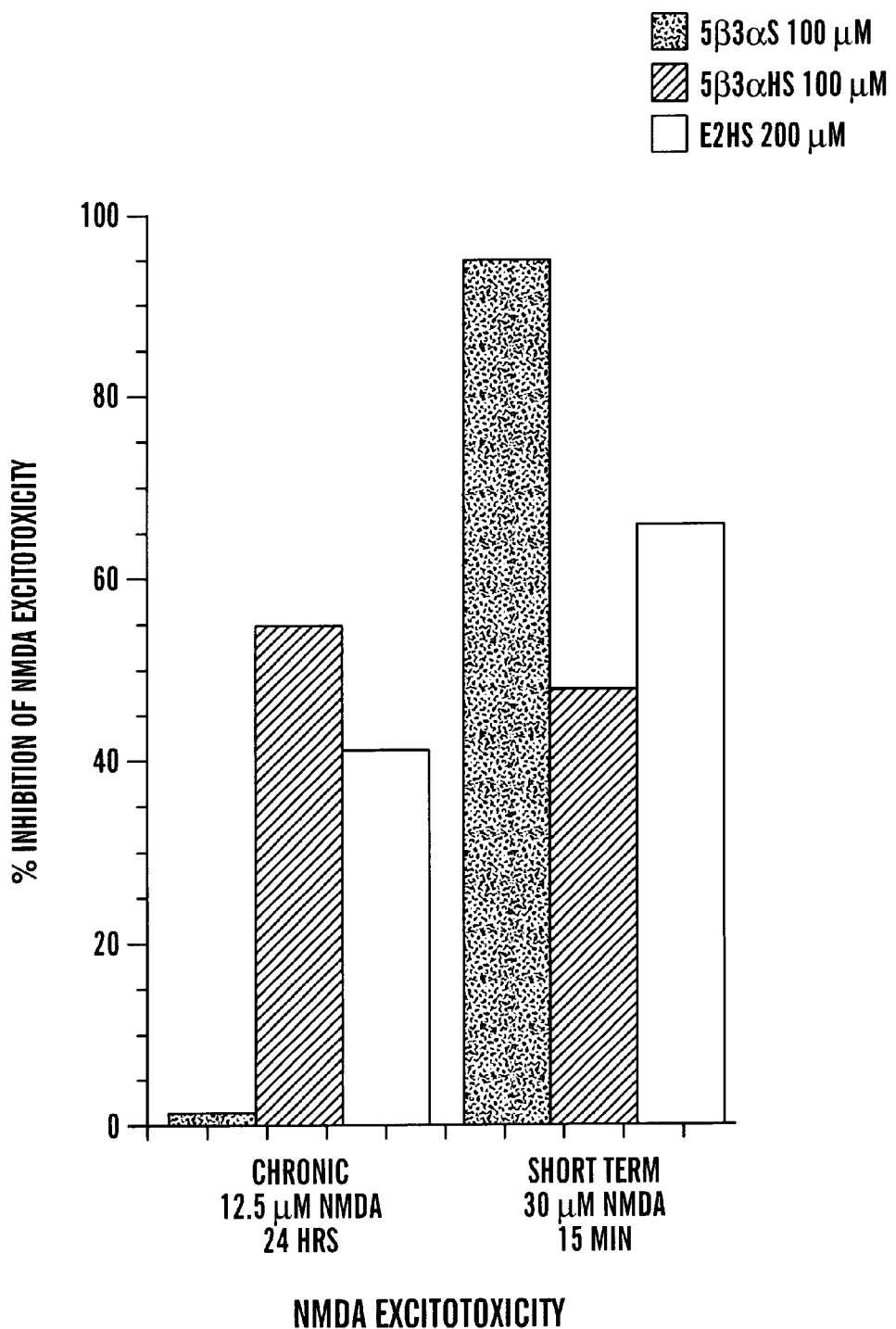
FIG. 5 is a bar graph of % inhibition of NMDA excitotoxicity (chronic and short term).
Figure 6A:
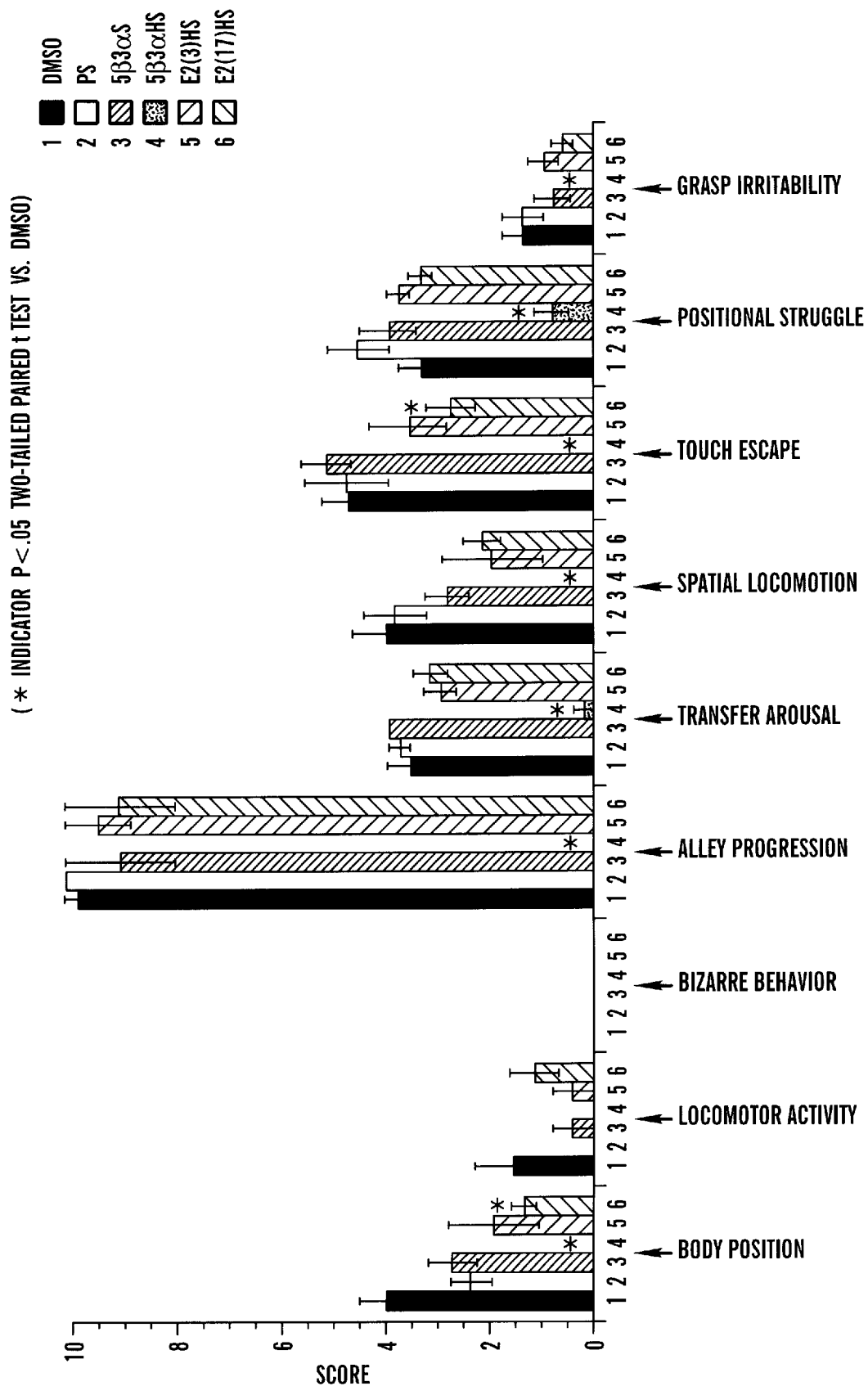
FIGS. 6A–6E are bar graphs of the behavior characteristics observed in mice injected with steroids.
Figure 6B:
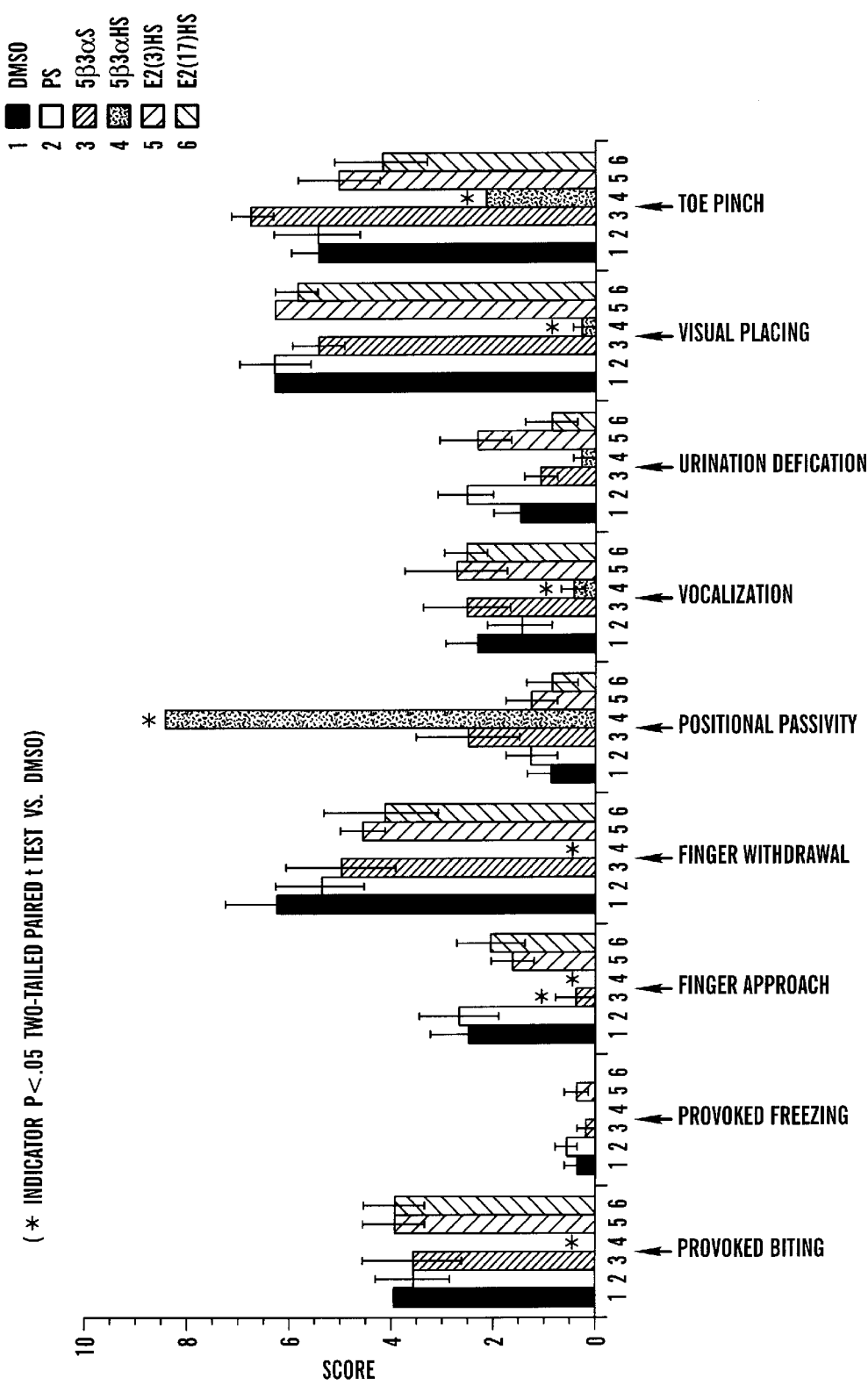
Figure 6C:
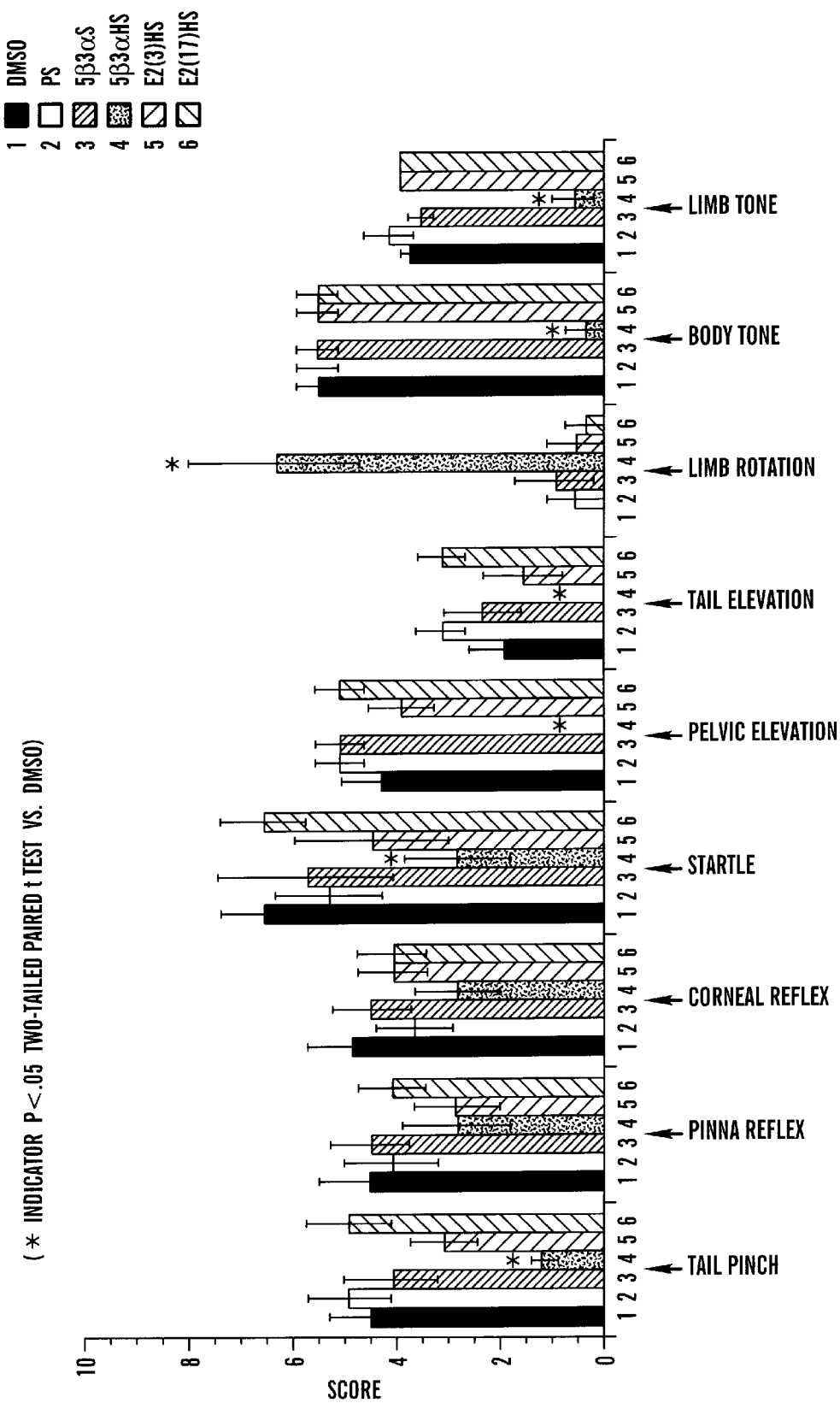
Figure 6D:
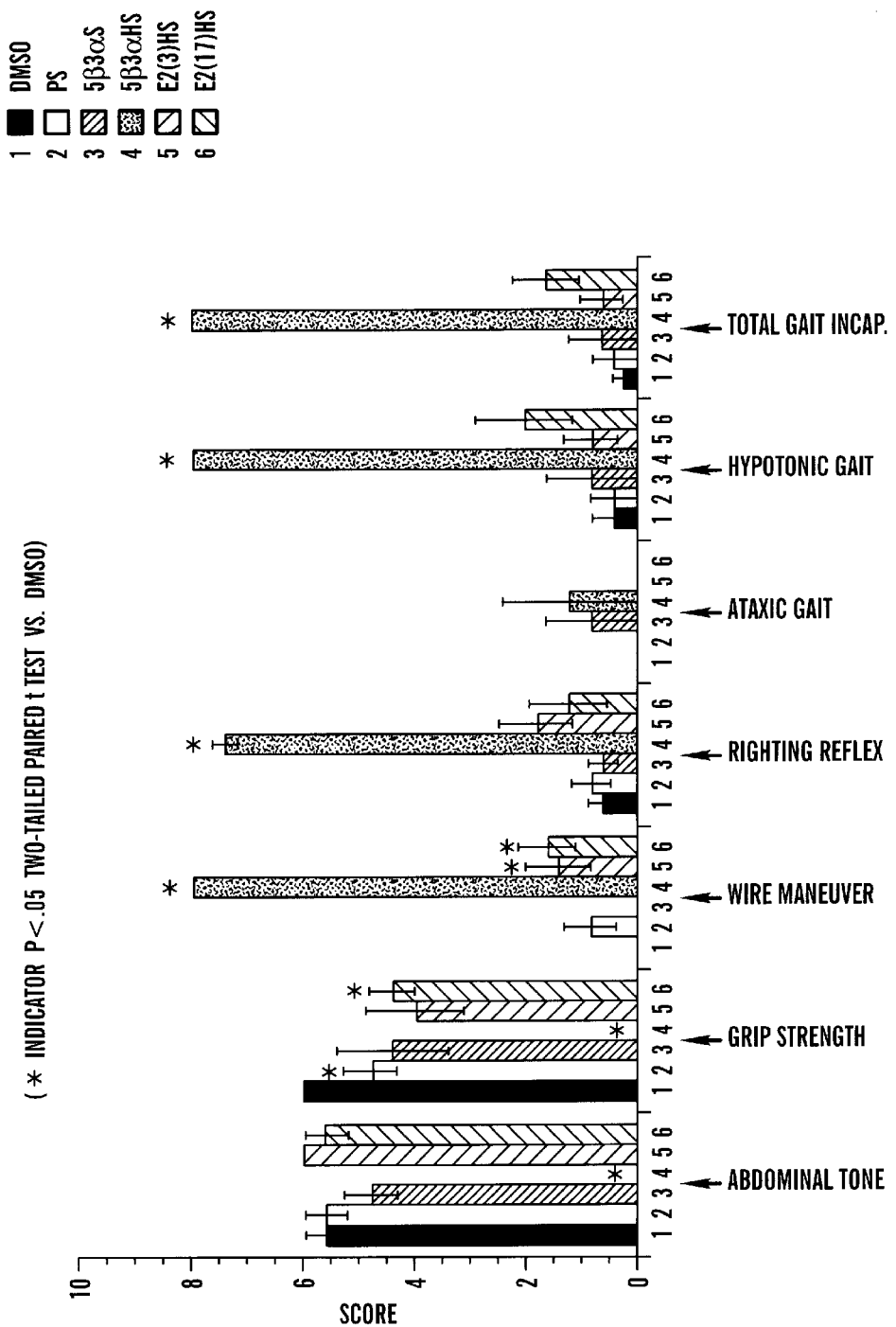
Figure 6E:
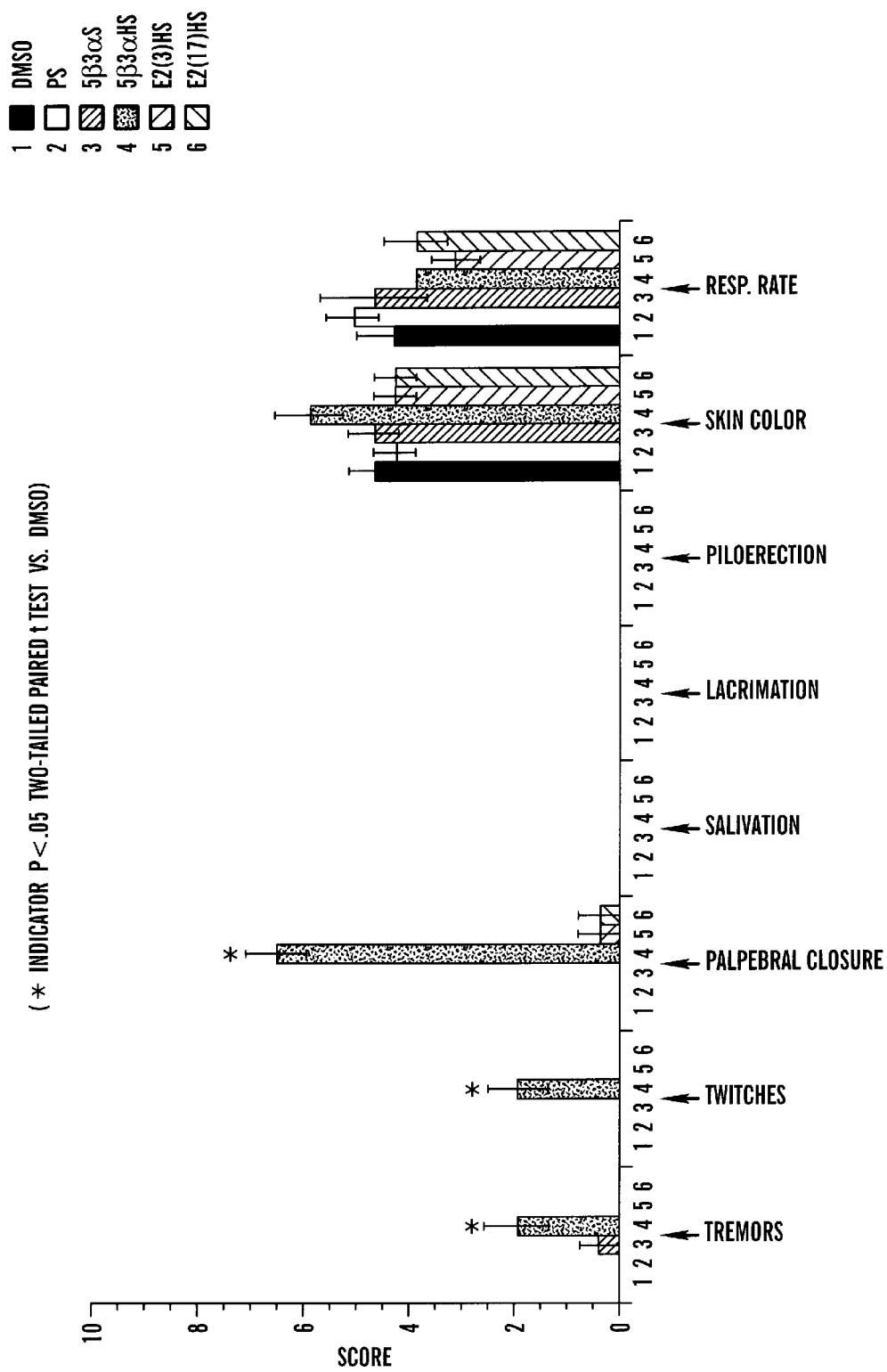

The results are illustrated in FIG. 5. 5β3αS protects against short term NMDA excitotoxicity but is ineffective against chronic NMDA-induced cell death. This may be due to instability of this compound. On occasion 5β3αS did show protection in the chronic exposure experiments but on average there was no effect.

5β3αS completely blocked the cell death due to NMDA when present during the exposure only, and was considerably less effective when present only after the exposure suggesting that protection is through a direct action on NMDA receptors. During and after as well as before, during, and after application of 5β3αS showed similar protection to the during only application.

5β3α hemisuccinate and 17β-estradiol hemisuccinate inhibit 50 and 40 percent of the cell death induced by chronic NMDA, and 46 and 65 percent of the cell death produced by short term exposure to NMDA. For both of these steroids more protection was seen in the excitotoxicity studies than might have been indicated by electrophysiology.

In addition, both of these steroids were most effective when present during NMDA exposure in the short term experiments. When present both during and after the NMDA insult the protection was somewhat less.

EXAMPLE 5

Modulation of Spontaneous Excitatory Postsynaptic Currents (EPSCs) by Pregnenolone Sulfate and its Derivatives in Cultured Neurons Whether the modulatory effects described herein would translate into modulation of synaptic responses, where the period of exposure of brief duration and localized to synaptic receptors, was examined.

Primary cultures of hippocampal neurons were prepared from embryonic day 18 rats. Cultured neurons were used in experiments 2–3 weeks after plating.

Spontaneous excitatory postsynaptic currents were recorded by the whole-cell variant of the patch clamp technique. The pipet solution usually contained (in mM) KCl 10, EGTA 11, sodium gluconate 3, potassium gluconate 140 and HEPES 10, adjusted to pH 7.2 with KOH. The bath solution contained (in mM) NaCl 150, KCl 4, $CaCl_2$ 1, and HEPES 10, adjusted to pH 7.2 with NaOH. Because NMDA-induced currents are subject to voltage-dependent block by extracellular $Mg^{2+}$, no magnesium salts were added to the bath solution. All records were made with the cell membrane potential clamped at −70 mV, which is very close to the Cl- equilibrium potential. Therefore, IPSCs are not expected to be observed and spontaneous activity should consist of EPSCs. The complete blockage of spontaneous activity by the co-application of the NMDA receptor antagonist APV and the non-NMDA receptor antagonist DNQX argues that the observed spontaneous activity is glutamate receptor-mediated.

Drug solutions were applied to single neurons by pressure ejection (15 psi) from 7-barrel pipets (tip opening ~3–5 μm) positioned ~50 μm from the neuronal soma. In all experiments, neurons received a 40s application of either steroid or steroid plus antagonist(s), followed by 10–20s pulse of external buffer solution.

Results

As shown in Table 3, PS potentiates spontaneous EPSCs, and 5βαS inhibits spontaneous EPSCs, in cultures of rat hippocampal neurons. The analogue of PS, 11-keto PS has no effect on EPSCs. The percentage potentiation produced by 100 μM 11-keto PS is 19±15% (n=4). This suggests that the effect of PS on EPSCs is specific. The effect of some metabolites of PS were also examined on EPSCs.

Most of embryonic rat hippocampal neurons maintained in cell culture and assayed between 10–21 days after plating exhibit spontaneous excitatory postsynaptic currents (EPSCs) in the $Mg^{2+}$ free extracellular solution. The endogenous neurosteroid pregnenolone sulfate potentiates reversibly EPSCs in primary cultures of voltage-clamped rat hippocampal neurons. The effect of EPSCs is dose-dependent, with an $EC_{50}$ of 11.9 μM and maximal potentiation of 223%. When EPSCs mediated by NMDA receptors are blocked with the specific NMDA receptor antagonist APV, the potentiation of EPSCs by PS is reduced. Conversely, when EPSCs mediated by non-NMDA glutamate receptors are blocked with the specific non-NMDA receptor antagonist DNQX, PS produces a greater potentiation of ESCs. These results indicate that PS primarily potentiates EPSCs mediated by NMDA receptors. The effects of PS on EPSCs agree with those of PS on the response induced by exogenously applied NMDA. These observations provide further evidence that neurosteroids such as PS have direct neuromodulatory effects on excitatory synaptic transmission in the CNS. This is the first demonstration of modulation of excitatory synaptic currents by neurosteroids.

EXAMPLE 6

Behavioral Effects of Sulfated and Succinylated Steroids

To test for behavioral effects, PS, 5β3αS, 5β3αHS, βE$_2$(17)HS, or βE$_2$(3)HS (7 mg/ml in DMSO) was administered to mice i.p. at 25 mg/kg (5 animals per drug group). Behavioral assessments were made 30 min. after injection using a comprehensive observational assessment of motor-affective responses, sensory-motor responses, posture, muscle tone, equilibration, CNS excitation, and autonomic function (Irwin, R. P., et al., *NeuroSci. Lett.*, 141:30–44 (1968)). 5β3αHS-treated animals lost virtually all muscle tone but retained to a moderate degree their startle, pina, and corneal reflexes. The latency to loss of righting reflex was 2.5±0.5 min., and the latency to regain the righting reflex was 83±11 min. The rapidity of onset argues that 5β3αHS readily crosses the blood brain barrier. Animals receiving PS were unaffected except for a single decreased score on locomotor activity. 5β3αS, βE$_2$(17)HS, and βE$_2$(3)HS treated mice showed very minor behavioral impairment. See FIGS. 6A–6E.

EXAMPLE 7

NMDA-induced Seizure and Death

5β3αHS (25 mg/kg, i.p.) protects mice from NMDA-induced death. None of the steroids tested altered the latency to NMDA-induced seizure. However, 100% of the animals that received 5β3αHS survived the 100 mg/kg NMDA challenge compared to 50% for DMSO, 75% for 5β3αS and E$_2$(3)HS, and 50% for E$_2$(17)HS.

EXAMPLE 8

Neuroprotection in vivo

5β3αHS was most active in the behavioral assay, suggesting that it penetrates the blood/brain barrier more readily than steroid sulfates. 5β3αHS was therefore selected for testing as a possible neuroprotective agent in vivo. As described below, 5β3αS increases the latency to onset of seizures and decreases mortality in rats following i.v. injection of 200 mg/kg NMDA. In the rat middle cerebral artery occlusion model of focal ischemia (Shiraishi, K. and Simon, R. P., *J. Neurosci. Meth*, 30:169–174 (1989)) cortical infarct volume was markedly reduced when i.v. infusion of 5β3αHS was initiated 5 min. after onset of ischemia. As compared to vehicle treated rats (n=9), 5β3αHS treated rats (n=10) exhibited a 47±10% reduction in cortical infarct volume and a 26±6% reduction in subcortical infarct volume. Cortical infarct volume was also significantly reduced when i.v. infusion of 5β3αHS was delayed until 30 min. after initiation of ischemia.

Materials and Methods
THE FORMALIN PAW LICK ANALGESIC TEST

Male CD-1 mice (Charles River laboratories, Wilmington, Mass.) weighing 20–25 g were used for the formalin test. Mice were injected intraperitoneally with the test compound dissolved in DMSO or with vehicle. Five minutes later 20 μl of 1% formalin was injected into the hind paw of each mouse. The time spent licking the injected paw was monitored for 25 minutes. The early phase of response was between 0–5 minutes and the late phase response was defined as the response between 5–25 minutes.

The NMDA-induced Convulsion Test in Mice

Male CD-1 mice (Charles River Laboratories, Wilmington, Mass.) weighing 20–25 g were used for the NMDA-induced convulsion test. Mice were injected intraperitoneally with the test compound dissolved in DMSO or with vehicle. NMDA (200 mg/kg, i.p.) was injected either 2 minutes after intravenous injection of test compound or 20 minutes after intraperitoneal injection of test compound. Mice were observed for tonic seizures and mortality with a time limit of 30 minutes. Mice which did not experience seizures or mortality beyond 30 minutes were scored as having a latency of 30 minutes.

The Middle Cerebral Artery Occlusion Cerebral Ischemia Test in Rats

Male Wistar rats (200–250 g) were used. Anesthesia was induced with 3% halothane in 70% nitrogen balanced with oxygen. Rats were intubated and artificially ventilated with 2% halothane in a mixture of 30% oxygen and 70% nitrogen. Body temperature was maintained at 37.5° C. during surgery by means of a warming pad with a rectal probe connected to a feedback control unit. Both common carotid arteries (CCA) were isolated, and a loose silk ligature was placed around each artery. A vertical skin incision was made between the left orbit and the auditory canal. Under constant saline irrigation the posterior part of the zygoma was removed and a small opening (2.0/2.5 mm) drilled dorso-rostrally to the foramen ovale. The dura was opened with a microsurgical hook and the brain gently retracted with a small spatula to expose the bifurcation of the internal carotid artery and middle cerebral artery. After permanent ligation of the ipsilateral CCA, the middle cerebral artery (MCA) was coagulated from its origin to the olfactory tract. The contralateral CCA was occluded for a period of 2 hours. A bolus intravenous injection (1 ml) of test compound dissolved in 5% DMSO, 10% 2-hydroxy propyl-β-cyclodextrin in 100 mM sodium phosphate buffer, pH 7.4, was given either immediately after MCA occlusion or 30 minutes after MCA occlusion. An intravenous infusion of the test drug in the same vehicle was initiated immediately after the bolus injection. Twenty-two hours after MCA occlusion rats were euthanized, and the brains were sectioned into 2 mm slices and stained with tetrazoliumred (2,3,5-triphenyl tetrazolium chloride). Areas of brain damage were assessed using an image analyzer with the NIH Image program, and the volumes of cortical and subcortical infarction were estimated by integration of areas in serial.

Results and Discussion

Figure 7:
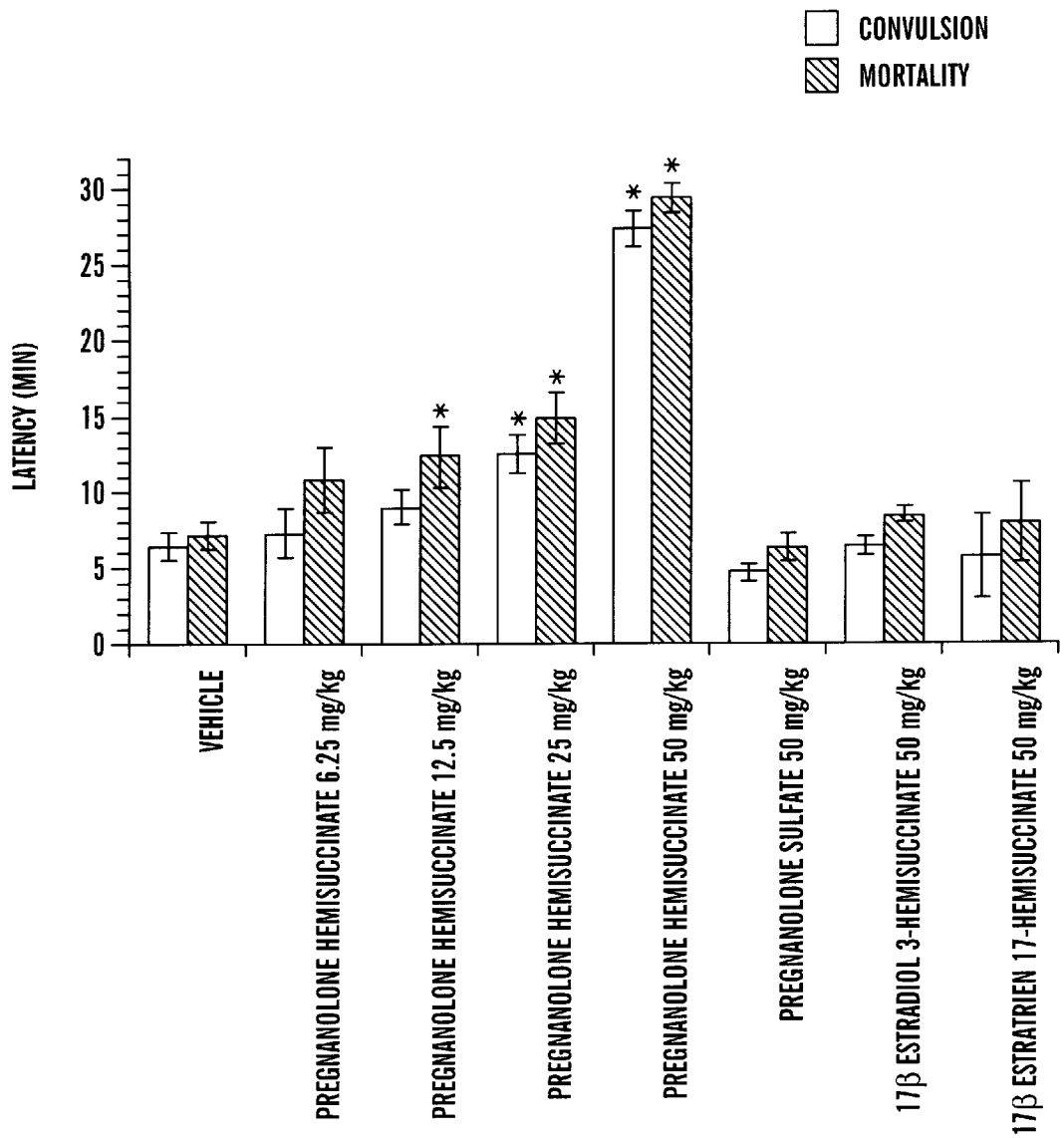
FIG. 7 is a histogram of data demonstrating the effect of pregnanolone hemisuccinate and related compounds, intraperitoneal (i.p.), on NMDA (200 mg/kg)-induced convulsion and mortality in mice.

As shown in FIG. 7, pregnenolone hemisuccinate dose-dependently inhibited tonic seizures induced by 200 mg/kg of NMDA. At the high dose, pregnanolone was able to completely block the seizures induced by NMDA up to the end test with a maximum time limit of 30 min. In the vehicle-treated group, NMDA induced tonic seizures in all the animals with a mean latency of less than 7 minutes.

Pregnanolone hemisuccinate dose-dependently inhibited mortality induced by 200 mg/kg of NMDA. At the high dose, pregnanolone was able to completely block the mortality induced by NMDA up to the end of the test with a maximum time limit of 30 min. In the vehicle-treated group, NMDA induced mortality in all animals with a mean latency of about 7 minutes.

Figure 8:
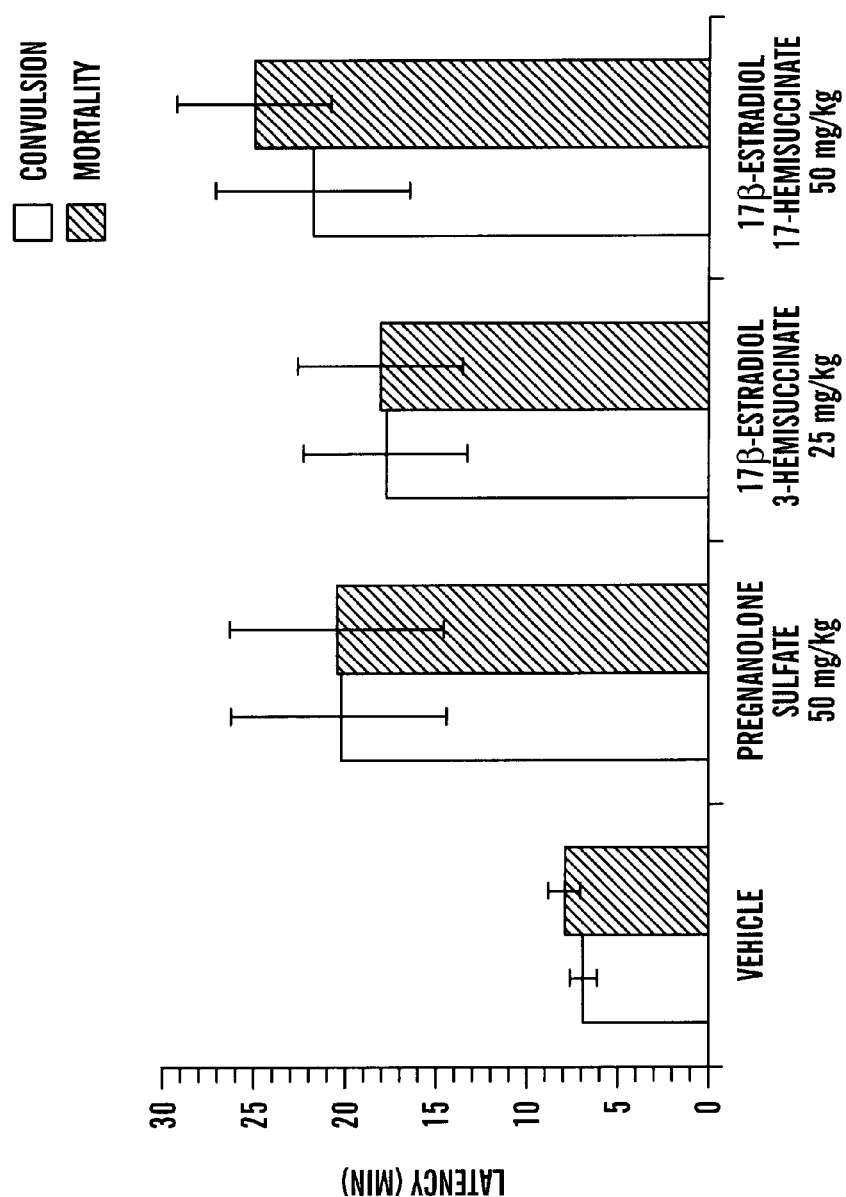
FIG. 8 is a histogram of data demonstrating the effect of intravenous (i.v.) administration of neuroactive steroids on NMDA-induced convulsion and mortality in mice.

As shown in FIG. 8, pregnanolone sulfate, 17β-estradiol 3-hemisuccinate, 17β-estradiol and 17-hemisuccinate were effective in blocking seizures and mortality induced by NMDA.

Figure 9A:
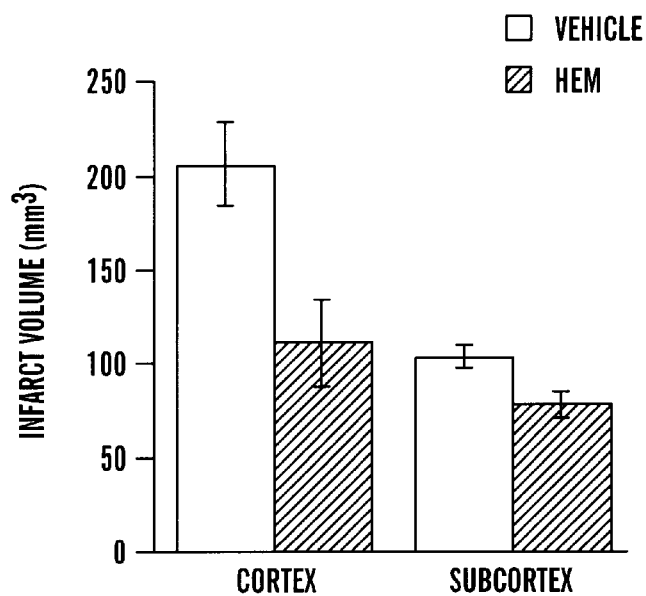
FIG. 9A is a histogram of data demonstrating the neuroprotective effect of 5β-pregnan-3α-ol-20-one hemisuccinate administered immediately after middle cerebral artery (MCA) occlusion.
Figure 9B:
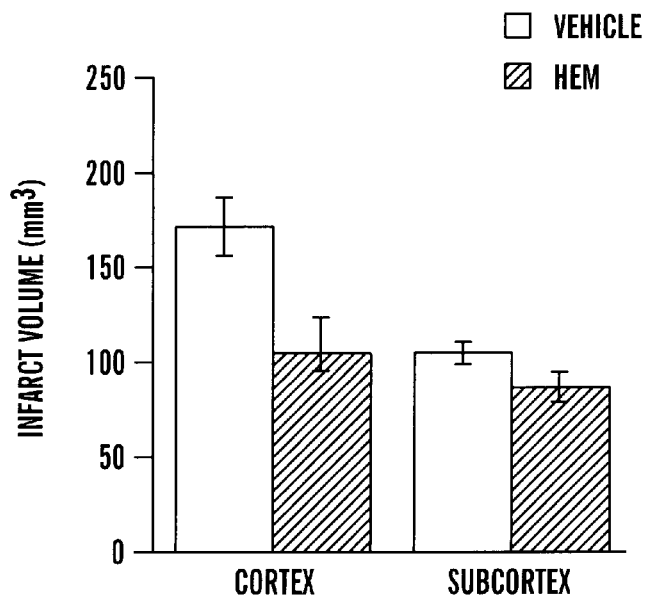
FIG. 9B is a histogram of data demonstrating the neuroprotective effect of 5β-pregnan-3α-ol-20-one hemisuccinate administered 30 minutes after MCA occlusion.

Pregnanolone hemisuccinate produced significant neuroprotection in the MCAO cerebral ischemia model. The infarction volumes of the cortical and subcortical brain regions were significantly decreased by treatment immediately after cerebral ischemia. The infarction volume of the cortical brain region was significantly decreased even when treatment was delayed for 30 minutes after cerebral ischemia (See FIGS. 9A and 9B). Focal cerebral ischemia was induced in the left hemisphere of male rats by proximal coagulation of the middle cerebral artery. In addition, the ipsilateral common carotid artery was permanently occluded and the contralateral common carotid artery was occluded for 2 h. Five minutes after initiation of ischemia, rats were injected with an i.v. loading dose of 6.9 mg/kg 5β3αHS, followed by i.v. infusion of 5β3αHS at 6.9 mg/kg/h. Little or no sedation was observed at this dose. Control rats were treated with vehicle. Infusion of 5β3αHS was continued for an additional 20 h, at which time the rats were sacrificed, and their brains were sliced and stained with the vital stain 2,3,5 triphenyl tetrazolium Cl.

Figure 10A:
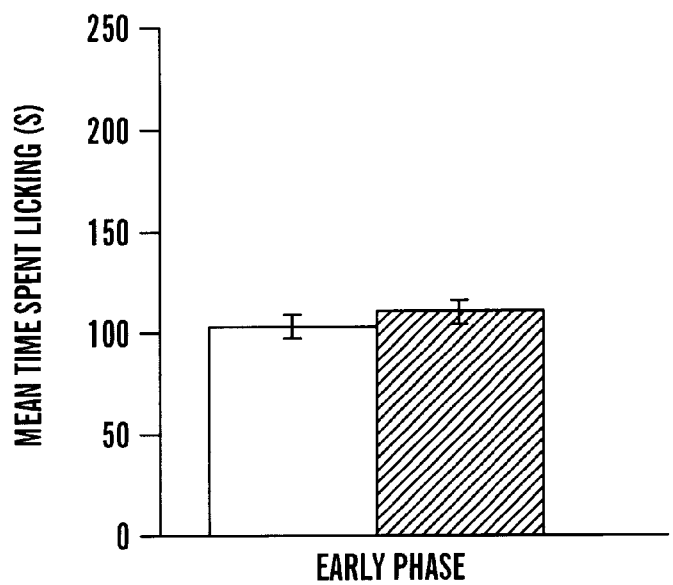
FIG. 10A is a histogram of data demonstrating the early phase effect of 5β-pregnan-3α-ol-20-one hemisuccinate (15 mg/kg) on formalin pain in the mouse.
Figure 10B:
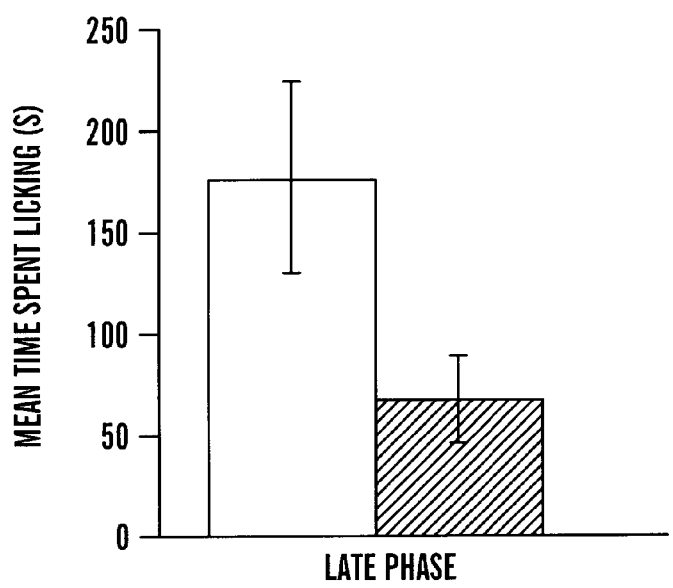
FIG. 10B is a histogram of data demonstrating the late phase effect of 5β-pregnan-3α-ol-20-one hemisuccinate (15 mg/kg) on formalin pain in the mouse.

Pregnanolone hemisuccinate was tested in the formalin-induced paw lick test in mice. Mice demonstrated a two phase response in this test. The early phase is related to acute pain induced by the injection of formalin into the paw, followed by period of no response and then a late phase of licking response which is believed to be related to more chronic pain. Pregnanolone had no effect on the early response but was effective in blocking the late phase response suggesting that pregnanolone may be effective in the treatment of chronic pain (FIGS. 10A and 10B).

The compounds of this invention have been demonstrated to antagonize the effect of glutamate on the NMDA receptor. These compounds also have been demonstrated to have significant effects for the treatment of epilepsy, chronic pain and stroke which are related to effects of excitatory amino acids including effects on the NMDA receptor. Thus, these compounds are useful for the treatment of neurotoxicity induced by excitatory amino acids. The neuroprotective effects of the compounds of the invention should offer protection against neurodegenerative diseases such as glaucoma, Huntington's disease, amyotrophic lateral sclerosis, AIDS dementia, Alzheimer's disease and Parkinson's disease. NMDA receptor antagonists have been shown to inhibit the development of tolerance to the analgesic effect of opioids. In addition, NMDA receptor antagonists have been shown to inhibit the development of physical dependence or repeated administration of opioids such as morphine. Thus, the compounds of the invention will be useful to inhibit the tolerance to the analgesic effects of opioids as well as the physical dependence of opioid drug abuse.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. A method for inhibiting N-methyl-D-aspartate glutamate receptor mediated ion-channel activity in an individual in need thereof comprising administering an effective amount of a compound selected from the group consisting of 3α-hydroxy-16-imino-5β-17-aza-androstane-11-one, 3α-hydroxy-5α-pregnane-11,20-dione hemisuccinate, pregnanolone sulfate, pregnanalone hemisuccinate, pregnenolone phosphate, pregnenolone formate, pregnenolone hemioxalate, pregnenolone hemimalonate, pregnenolone hemiglutarate, 20-oxopregn-5-en-3β-yl carboxymethyl ether, 3α-hydroxypregn-5-en-20-one sulfate, 3-hydroxy-19-norpregna-1,3,5(10)-trien-20-one, 3-hydroxy-19-norpregna-1,3,5(10), 6,8-pentaen-20-one, 17α-isopregnenolone sulfate, 17-acetoxypregnenolone sulfate, 21-hydroxypregnenolone sulfate, 20β-acetoxy-3β-hydroxypregn-5-ene-sulfate, pregnenolone sulfate 20-ethyleneketal, pregnenolone sulfate 20-carboxymethyloxime, 20-deoxypregnenolone sulfate, 21-acetoxy-17-hydroxypregnenolone sulfate, 17-propyloxypregnenolone sulfate, 17-butyloxypregnenolone sulfate, pyridinium, imidazolium, 6-methylpregnenolone sulfate, 6,16α-dimethylpregnenolone sulfate, 3β-hydroxy-5β-pregnan-20-one sulfate, 3β-hydroxy-6-methylpregna-5,16-dien-20-one sulfate, 3β-hydroxy-6,16-dimethylpregna-5,16-dien-20-one sulfate, 3β-hydroxypregna-5,16-dien-20-one sulfate, diosgenin sulfate, 3β-hydroxyandrost-5-en-17β-carboxylic acid methyl ester sulfate, 3α-hydroxy-5α-pregnan-20-one sulfate, 3α-hydroxy-5β-pregnan-20-one sulfate, 3α-hydroxy-5β-pregnan-20-one formate, 3α-hydroxy-5β-pregnan-20-one hemioxalate, 3α-hydroxy-5β-pregnan-20-one hemimalonate, 3α-hydroxy-5β-pregnan-20-one hemisuccinate, 3α-hydroxy-5β-pregnan-20-one hemiglutarate, estradiol-3-formate, estradiol-3-hemioxalate, estradiol-3-hemimalonate, estradiol-3-hemisuccinate, estradiol-3-hemiglutarate, estradiol-17-methyl ether, estradiol-17-formate, estradiol-17-hemioxalate, estradiol-17-hemimalonate, estradiol-17-hemisuccinate, estradiol-17-hemiglutarate, estradiol 3-methyl ether, 17β-estradiol-3-hemisuccinate, 17-deoxyestrone, 17β-hydroxyestra-1,3,5 (10)-trien-3-yl carboxymethyl ether, 11β-OH-pregnanolone sulfate, and androsterone sulfate.

2. A method for inhibiting the toxic effects associated with activation of the N-methyl-D-aspartate receptor in neurons in an individual in need thereof, comprising administering an effective amount of a compound selected from the group consisting of 3α-hydroxy-16-imino-5β-17-aza-androstane-11-one, 3α-hydroxy-5α-pregnane-11,20-dione hemisuccinate, pregnanolone sulfate, pregnanalone hemisuccinate, pregnenolone phosphate, pregnenolone formate, pregnenolone hemioxalate, pregnenolone hemimalonate, pregnenolone hemiglutarate, 20-oxopregn-5-en-3β-yl carboxymethyl ether, 3α-hydroxypregn-5-en-20-one sulfate, 3-hydroxy-19-norpregna-1,3,5(10)-trien-20-one, 3-hydroxy-19-norpregna-1,3,5(10), 6,8-pentaen-20-one, 17α-isopregnenolone sulfate, 17-acetoxypregnenolone sulfate, 21-hydroxypregnenolone sulfate, 20β-acetoxy-3β-hydroxypregn-5-ene-sulfate, pregnenolone sulfate 20-ethyleneketal, pregnenolone sulfate 20-carboxymethyloxime, 20-deoxypregnenolone sulfate, 21-acetoxy-17-hydroxypregnenolone sulfate, 17-propyloxypregnenolone sulfate, 17-butyloxypregnenolone sulfate, pyridinium, imidazolium, 6-methylpregnenolone sulfate, 6,16α-dimethylpregnenolone sulfate, 3β-hydroxy-5β-pregnan-20-one sulfate, 3β-hydroxy-6-methylpregna-5,16-dien-20-one sulfate, 3β-hydroxy-6,16-dimethylpregna-5,16-dien-20-one sulfate, 3β-hydroxypregna-5,16-dien-20-one sulfate, diosgenin sulfate, 3β-hydroxyandrost-5-en-17β-carboxylic acid methyl ester sulfate, 3α-hydroxy-5α-pregnan-20-one sulfate, 3α-hydroxy-5β-pregnan-20-one sulfate, 3α-hydroxy-5β-pregnan-20-one formate, 3α-hydroxy-5β-pregnan-20-one hemioxalate, 3α-hydroxy-5β-pregnan-20-one hemimalonate, 3α-hydroxy-5β-pregnan-20-one hemisuccinate, 3α-hydroxy-5β-pregnan-20-one hemiglutarate, estradiol-3-formate, estradiol-3-hemioxalate, estradiol-3-hemimalonate, estradiol-3-hemisuccinate, estradiol-3-hemiglutarate, estradiol-17-methyl ether, estradiol-17-formate, estradiol-17-hemioxalate, estradiol-17-hemimalonate, estradiol-17-hemisuccinate, estradiol-17-hemiglutarate, estradiol 3-methyl ether, 17β-estradiol-3-hemisuccinate, 17-deoxyestrone, 17β-hydroxyestra-1,3,5(10)-trien-3-yl carboxymethyl ether, 11β-OH-pregnanolone sulfate, and androsterone sulfate.

3. A method of reducing neuronal cell death resulting from L-glutamate activation of the N-methyl-D-aspartate receptor in an individual in need thereof, comprising administering a compound selected from the group consisting of 3α-hydroxy-16-imino-5β-17-aza-androstane-11-one, 3α-hydroxy-5α-pregnane-11,20-dione hemisuccinate, pregnanolone sulfate, pregnanalone hemisuccinate, pregnenolone phosphate, pregnenolone formate, pregnenolone hemioxalate, pregnenolone hemimalonate, pregnenolone hemiglutarate, 20-oxopregn-5-en-3β-yl carboxymethyl ether, 3α-hydroxypregn-5-en-20-one sulfate, 3-hydroxy-19-norpregna-1,3,5(10)-trien-20-one, 3-hydroxy-19-norpregna-1,3,5(10), 6,8-pentaen-20-one, 17α-isopregnenolone sulfate, 17-acetoxypregnenolone sulfate, 21-hydroxypregnenolone sulfate, 20β-acetoxy-3β-hydroxypregn-5-ene-sulfate, pregnenolone sulfate 20-ethyleneketal, pregnenolone sulfate 20-carboxymethyloxime, 20-deoxypregnenolone sulfate, 21-acetoxy-17-hydroxypregnenolone sulfate, 17-propyloxypregnenolone sulfate, 17-butyloxypregnenolone sulfate, pyridinium, imidazolium, 6-methylpregnenolone sulfate, 6,16α-dimethylpregnenolone sulfate, 3β-hydroxy-5β-pregnan-20-one sulfate, 3β-hydroxy-6-methylpregna-5,16-dien-20-one sulfate, 3β-hydroxy-6,16-dimethylpregna-5,16-dien-20-one sulfate, 3β-hydroxypregna-5,16-dien-20-one sulfate, diosgenin sulfate, 3β-hydroxyandrost-5-en-17β-carboxylic acid methyl ester sulfate, 3α-hydroxy-5α-pregnan-20-one sulfate, 3α-hydroxy-5β-pregnan-20-one sulfate, 3α-hydroxy-5-pregnan-20-one formate, 3α-hydroxy-5β-pregnan-20-one hemioxalate, 3α-hydroxy-5β-pregnan-20-one hemimalonate, 3α-hydroxy-5β-pregnan-20-one hemisuccinate, 3α-hydroxy-5β-pregnan-20-one hemiglutarate, estradiol-3-formate, estradiol-3-hemioxalate, estradiol-3-hemimalonate, estradiol-3-hemisuccinate, estradiol-3-hemiglutarate, estradiol-17-methyl ether, estradiol-17-formate, estradiol-17-hemioxalate, estradiol-17-hemimalonate, estradiol-17-hemisuccinate, estradiol-17-hemiglutarate, estradiol 3-methyl ether, 17β-estradiol-3-hemisuccinate, 17-deoxyestrone, 17β-hydroxyestra-1,3,5(10)-trien-3-yl carboxymethyl ether, 11β-OH-pregnanolone sulfate, and androsterone sulfate.

4. A method of inhibiting excitatory glutamate-mediated synaptic activity of neuronal cells in an individual in need thereof comprising administering a compound selected from the group consisting of 3α-hydroxy-16-imino-5β-17-aza-androstane-11-one, 3α-hydroxy-5α-pregnane-11,20-dione hemisuccinate, pregnanolone sulfate, pregnanalone hemisuccinate, pregnenolone phosphate, pregnenolone formate, pregnenolone hemioxalate, pregnenolone hemimalonate, pregnenolone hemiglutarate, 20-oxopregn-5-en-3β-yl carboxymethyl ether, 3α-hydroxypregn-5-en-20-one sulfate, 3-hydroxy-19-norpregna-1,3,5(10)-trien-20-one, 3-hydroxy-19-norpregna-1,3,5(10), 6,8-pentaen-20-one, 17α-isopregnenolone sulfate, 17-acetoxypregnenolone sulfate, 21-hydroxypregnenolone sulfate, 20β-acetoxy-3β-hydroxypregn-5-ene-sulfate, pregnenolone sulfate 20-ethyleneketal, pregnenolone sulfate 20-carboxymethyloxime, 20-deoxypregnenolone sulfate, 21-acetoxy-17-hydroxypregnenolone sulfate, 17-propyloxypregnenolone sulfate, 17-butyloxypregnenolone sulfate, pyridinium, imidazolium, 6-methylpregnenolone sulfate, 6,16α-dimethylpregnenolone sulfate, 3β-hydroxy-5β-pregnan-20-one sulfate, 3β-hydroxy-6-methylpregna-5,16-dien-20-one sulfate, 3β-hydroxy-6,16-dimethylpregna-5,16-dien-20-one sulfate, 3β-hydroxypregna-5,16-dien-20-one sulfate, diosgenin sulfate, 3β-hydroxyandrost-5-en-17β-carboxylic acid methyl ester sulfate, 3α-hydroxy-5α-pregnan-20-one sulfate, 3α-hydroxy-5β-pregnan-20-one sulfate, 3α-hydroxy-5β-pregnan-20-one formate, 3α-hydroxy-5β-pregnan-20-one hemioxalate, 3α-hydroxy-5β-pregnan-20-one hemimalonate, 3α-hydroxy-5β-pregnan-20-one hemisuccinate, 3α-hydroxy-5β-pregnan-20-one hemiglutarate, estradiol-3-formate, estradiol-3-hemioxalate, estradiol-3-hemimalonate, estradiol-3-hemisuccinate, estradiol-3-hemiglutarate, estradiol-17-methyl ether, estradiol-17-formate, estradiol-17-hemioxalate, estradiol-17-hemimalonate, estradiol-17-hemisuccinate, estradiol-17-hemiglutarate, estradiol 3-methyl ether, 17β-estradiol-3-hemisuccinate, 17-deoxyestrone, 17β-hydroxyestra-1,3,5(10)-trien-3-yl carboxymethyl ether, 11β-OH-pregnanolone sulfate, and androsterone sulfate.

5. A method of treating a disease selected from the group consisting of neuropathic pain, drug withdrawal/dependency, epilepsy, glaucoma, chronic neurodegenerative diseases, amyotrophic lateral sclerosis, anxiety disorders, brain cell death, ischaemia, stroke, and trauma in an individual when said disease results from L-glutamate-induced NMDA receptor activation, comprising administering to the individual an effective amount of a compound selected from the group consisting of 3α-hydroxy-16-imino-5β-17-aza-androstane-11-one, 3α-hydroxy-5α-pregnane-11,20-dione hemisuccinate, pregnanolone sulfate, pregnanalone hemisuccinate, pregnenolone phosphate, pregnenolone formate, pregnenolone hemioxalate, pregnenolone hemimalonate, pregnenolone hemiglutarate, 20-oxopregn-5-en-3β-yl carboxymethyl ether, 3α-hydroxypregn-5-en-20-one sulfate, 3-hydroxy-19-norpregna-1,3,5(10)-trien-20-one, 3-hydroxy-19-norpregna-1,3,5(10), 6,8-pentaen-20-one, 17α-isopregnenolone sulfate, 17-acetoxypregnenolone sulfate, 21-hydroxypregnenolone sulfate, 20β-acetoxy-3β-hydroxypregn-5-ene-sulfate, pregnenolone sulfate 20-ethyleneketal, pregnenolone sulfate 20-carboxymethyloxime, 20-deoxypregnenolone sulfate, 21-acetoxy-17-hydroxypregnenolone sulfate, 17-propyloxypregnenolone sulfate, 17-butyloxypregnenolone sulfate, pyridinium, imidazolium, 6-methylpregnenolone sulfate, 6,16α-dimethylpregnenolone sulfate, 3β-hydroxy-5β-pregnan-20-one sulfate, 3β-hydroxy-6-methylpregna-5,16-dien-20-one sulfate, 3β-hydroxy-6,16-dimethylpregna-5,16-dien-20-one sulfate, 3β-hydroxypregna-5,16-dien-20-one sulfate, diosgenin sulfate, 3β-hydroxyandrost-5-en-17β-carboxylic acid methyl ester sulfate, 3α-hydroxy-5α-pregnan-20-one sulfate, 3α-hydroxy-5β-pregnan-20-one sulfate, 3α-hydroxy-5β-pregnan-20-one formate, 3α-hydroxy-5β-pregnan-20-one hemioxalate, 3α-hydroxy-5β-pregnan-20-one hemimalonate, 3α-hydroxy-5β-pregnan-20-one hemisuccinate, 3α-hydroxy-5β-pregnan-20-one hemiglutarate, estradiol-3-formate, estradiol-3-hemioxalate, estradiol-3-hemimalonate, estradiol-3-hemisuccinate, estradiol-3-hemiglutarate, estradiol-17-methyl ether, estradiol-17-formate, estradiol-17-hemioxalate, estradiol-17-hemimalonate, estradiol-17-hemisuccinate, estradiol-17-hemiglutarate, estradiol 3-methyl ether, 17β-estradiol-3-hemisuccinate, 17-deoxyestrone, 17β-hydroxyestra-1,3,5 (10)-trien-3-yl carboxymethyl ether, 11β-OH-pregnanolone sulfate, and androsterone sulfate.

6. A method of inhibiting the excitatory glutamate-mediated synaptic activity in an individual in need thereof, comprising administering to the individual a compound selected from the group consisting of 3α-hydroxy-16-imino-5β-17-aza-androstane-11-one, 3α-hydroxy-5α-pregnane-11,20-dione hemisuccinate, pregnanolone sulfate, pregnanalone hemisuccinate, pregnenolone phosphate, pregnenolone formate, pregnenolone hemioxalate, pregnenolone hemimalonate, pregnenolone hemiglutarate, 20-oxopregn-5-en-3β-yl carboxymethyl ether, 3α-hydroxypregn-5-en-20-one sulfate, 3-hydroxy-19-norpregna-1,3,5(10)-trien-20-one, 3-hydroxy-19-norpregna-1,3,5(10), 6,8-pentaen-20-one, 17α-isopregnenolone sulfate, 17-acetoxypregnenolone sulfate, 21-hydroxypregnenolone sulfate, 20β-acetoxy-3β-hydroxypregn-5-ene-sulfate, pregnenolone sulfate 20-ethyleneketal, pregnenolone sulfate 20-carboxymethyloxime, 20-deoxypregnenolone sulfate, 21-acetoxy-17-hydroxypregnenolone sulfate, 17-propyloxypregnenolone sulfate, 17-butyloxypregnenolone sulfate, pyridinium, imidazolium, 6-methylpregnenolone sulfate, 6,16α-dimethylpregnenolone sulfate, 3β-hydroxy-5β-pregnan-20-one sulfate, 3β-hydroxy-6-methylpregna-5,16-dien-20-one sulfate, 3β-hydroxy-6,16-dimethylpregna-5,16-dien-20-one sulfate, 3β-hydroxypregna-5,16-dien-20-one sulfate, diosgenin sulfate, 3β-hydroxyandrost-5-en-17β-carboxylic acid methyl ester sulfate, 3α-hydroxy-5α-pregnan-20-one sulfate, 3α-hydroxy-5β-pregnan-20-one sulfate, 3α-hydroxy-5β-pregnan-20-one formate, 3α-hydroxy-5β-pregnan-20-one hemioxalate, 3α-hydroxy-5β-pregnan-20-one hemimalonate, 3α-hydroxy-5β-pregnan-20-one hemisuccinate, 3α-hydroxy-5β-pregnan-20-one hemiglutarate, estradiol-3-formate, estradiol-3-hemioxalate, estradiol-3-hemimalonate, estradiol-3-hemisuccinate, estradiol-3-hemiglutarate, estradiol-17-methyl ether, estradiol-17-formate, estradiol-17-hemioxalate, estradiol-17-hemimalonate, estradiol-17-hemisuccinate, estradiol-17-hemiglutarate, estradiol 3-methyl ether, 17β-estradiol-3-hemisuccinate, 17-deoxyestrone, 17β-hydroxyestra-1,3,5 (10)-trien-3-yl carboxymethyl ether, 11β-OH-pregnanolone sulfate, and androsterone sulfate, wherein the compound functions as an agent selected from the group consisting of an anti-convulsant agent, a sedative agent and a muscle relaxant.

7. A method of claim 1, wherein the compound is selected from the group consisting of: 3α-hydroxy-5β-pregnan-20-one sulfate, 3β-hydroxy-5β-pregnan-20-one sulfate, 3α-hydroxy-5α-pregnan-20-one sulfate, 3α-hydroxy-5β-pregnan-20-one hemisuccinate, 3α-hydroxy-5α-pregnan-20-one hemisuccinate, 3β-hydroxy-5β-pregnan-20-one hemisuccinate, 17β-estradiol-3-hemisuccinate, 17β-estradiol-17-hemisuccinate, 17β-estradiol-3,17-di-hemisuccinate, 17β-estradiol, androsterone sulfate and 11β-OH-pregnenolone sulfate.

8. A method of claim 1, wherein the effective amount is a concentration of from about 1 to about 500 μM.

9. A method of claim 8, wherein the effective amount is from about 50 to about 250 μM.

10. The method of claim 2, wherein the compound is selected from the group consisting of: 3α-hydroxy-5β-pregnan-20-one sulfate, 3β-hydroxy-5β-pregnan-20-one sulfate, 3α-hydroxy-5α-pregnan-20-one sulfate, 3α-hydroxy-5β-pregnan-20-one hemisuccinate, 3α-hydroxy-5α-pregnan-20-one hemisuccinate, 3β-hydroxy-5β-pregnan-20-one hemisuccinate, 17β-estradiol-3-hemisuccinate, 17β-estradiol-17-hemisuccinate, 17β-estradiol-3,17-di-hemisuccinate, 17β-estradiol, androsterone sulfate and 11β-OH-pregnenolone sulfate.

11. The method of claim 2, wherein the effective amount is a concentration of from about 1 to about 500 μM.

12. The method of claim 11, wherein the effective amount is from about 50 to about 250 μM.

13. The method of claim 10, wherein the neurons are selected from the group consisting of: hippocampal cells and spinal cord cells.

14. The method of claim 3, wherein the compound is selected from the group consisting of: 3α-hydroxy-5β-pregnan-20-one sulfate, 3β-hydroxy-5β-pregnan-20-one sulfate, 3α-hydroxy-5α-pregnan-20-one sulfate, 3α-hydroxy-5β-pregnan-20-one hemisuccinate, 3α-hydroxy-5α-pregnan-20-one hemisuccinate, 3β-hydroxy-5β-pregnan-20-one hemisuccinate, 17β-estradiol-3-hemisuccinate, 17β-estradiol-17-hemisuccinate, 17β-estradiol-3,17-di-hemisuccinate, 17β-estradiol, androsterone sulfate and 11β-OH-pregnenolone sulfate.

15. The method of claim 3, wherein the effective amount is a concentration of from about 1 to about 500 μM.

16. The method of claim 5, wherein the compound is 3α-hydroxy-5β-pregnan-20-one hemisuccinate.

17. The method of claim 5, wherein the compound is selected from the group consisting of: 3α-hydroxy-5α-pregnan-20-one sulfate, 11β-OH-pregnenolone sulfate, and 17β-estradiol hemisuccinate.

18. The method of claim 5, wherein the compound is used at a concentration of from about 1 to about 500 μM.

19. The method of claim 18, wherein the concentration is from about 50 to about 250 μM.

* * * * *

UNITED STATES PATENT AND TRADEMARK OFFICE
CERTIFICATE OF CORRECTION

PATENT NO. : 6,083,941
DATED : July 4, 2000
INVENTOR(S) : David H. Farb

It is certified that error appears in the above-identified patent and that said Letters Patent is hereby corrected as shown below:

Column 1,
Line 22, insert -- <u>Government Support</u>
This invention was made with government support under Contract No. MH-49469 awarded by the National Institutes of Health. The government has certain rights in the invention. --

Signed and Sealed this

Sixth Day of November, 2001

Attest:

*Attesting Officer*

NICHOLAS P. GODICI
*Acting Director of the United States Patent and Trademark Office*